(12) United States Patent
Dickey et al.

(10) Patent No.: US 9,045,434 B1
(45) Date of Patent: Jun. 2, 2015

(54) COMPOSITIONS AND METHODS OF TREATMENT FOR MYOCILIN GLAUCOMA BY SELECTIVELY INHIBITING GRP94

(71) Applicants: Chad Anthony Dickey, Tampa, FL (US); Amirthaa Suntharalingam, Tampa, FL (US); Brian S. J. Blagg, Lawrence, KS (US)

(72) Inventors: Chad Anthony Dickey, Tampa, FL (US); Amirthaa Suntharalingam, Tampa, FL (US); Brian S. J. Blagg, Lawrence, KS (US)

(73) Assignees: University of South Florida, Tampa, FL (US); The University of Kansas, Lawrence, KS (US)

( * ) Notice: Subject to any disclaimer, the term of this patent is extended or adjusted under 35 U.S.C. 154(b) by 0 days.

(21) Appl. No.: 14/083,031

(22) Filed: Nov. 18, 2013

Related U.S. Application Data

(60) Provisional application No. 61/727,561, filed on Nov. 16, 2012.

(51) Int. Cl.
| | | |
|---|---|---|
| A61K 31/4174 | (2006.01) | |
| A61P 27/06 | (2006.01) | |
| C07D 233/64 | (2006.01) | |

(52) U.S. Cl.
CPC .......... *C07D 233/64* (2013.01); *A61K 31/4174* (2013.01)

(58) Field of Classification Search
USPC ...................................... 514/400; 548/341.5
See application file for complete search history.

(56) References Cited

U.S. PATENT DOCUMENTS 8,685,966 B2    4/2014  Blagg et al.

OTHER PUBLICATIONS

Duerfeldt et al. "Development of a Grp94 inhibitor" J. Am. Chem. Soc. 2012, 134, 9796-9804.*
Suntharalingam et al. "Glucose-regulated Protein 94 Triage of Mutant Myocilin through Endoplasmic Reticulum-associated Degradation Subverts a More Efficient Autophagic Clearance Mechanism" J. Biol. Chem. 2012, 287, 40661-40669.*
Joe MK & Tomarev SI (2010) Expression of myocilin mutants sensitizes cells to oxidative stress-induced apoptosis: implication for glaucoma pathogenesis. Am J Pathol 176(6):2880-2890.
Kamal A, Boehm MF, & Burrows FJ (2004) Therapeutic and diagnostic implications of Hsp90 activation. Trends Mol Med 10(6):283-290.
Kim, Y. S. et al. Update on Hsp90 inhibitors in clinical trial. Curr. Top. Med. Chem. 9, 1479-1492, (2009).
Koga H & Cuervo AM (2011) Chaperone-mediated autophagy dysfunction in the pathogenesis of neurodegeneration. Neurobiol Dis 43(1):29-37.

Krukenberg, K. A., Southworth, D. R., Street, T. O. & Agard, D. A. pH-dependent conformational changes in bacterial Hsp90 reveal a Grp94-like conformation at pH 6 that is highly active in suppression of citrate synthase aggregation. J. Mol. Biol. 390, 278-291, (2009).
Krukenberg, K. A., Bottcher, U. M., Southworth, D. R. & Agard, D. A. Grp94, the endoplasmic reticulum Hsp90, has a similar solution conformation to cytosolic Hsp90 in the absence of nucleotide. Protein Sci. 18, 1815-1827, (2009).
Kwon YH, Fingert JH, Kuehn MH, & Alward WL (2009) Primary open-angle glaucoma. N. Engl. J. Med. 360 (11):1113-1124.
Lam DS, et al. (2000) Truncations in the TIGR gene in individuals with and without primary open-angle glaucoma. Invest Ophthalmol Vis Sci 41(6):1386-1391.
Li, Y., Schwartz, S. J. & Sun, D. New developments in Hsp90 inhibitors as anti-cancer therapeutics: mechanisms, clinical perspective and more potential. Drug Resist. Update 12, 17-27, (2009).
Liang, X. H., Jackson, S., Seaman, M., Brown, K., Kempkes, B., Hibshoosh, H., and Levine, B. (1999) Introduction of Autophagy and Inhibition of Tumorigenesis by beclin 1, Nature 402:672-676.
Liou B, et al. (2006) Analyses of variant acid beta-glucosidases: effects of Gaucher disease mutations. J Biol Chem 281(7):4242-4253.
Liton PB, Lin Y, Gonzalez P, & Epstein DL (2009) Potential role of lysosomal dysfunction in the pathogenesis of primary open angle glaucoma. Autophagy 5(1):122-124.
Liu X, Garriga P, & Khorana HG (1996) Structure and function in rhodopsin: correct folding and misfolding in two point mutants in the intradiscal domain of rhodopsin identified in retinitis pigmentosa. Proc Natl Acad Sci US A 93 (10):4554-4559.
Liu Y & Vollrath D (2004) Reversal of mutant myocilin non-secretion and cell killing: implications for glaucoma. Hum Mol Genet 13(11):1193-1204.
Liu Y, Sweet DT, Irani-Tehrani M, Maeda N, & Tzima E (2008) Shc coordinates signals from intercellular junctions and integrins to regulate flow-induced inflammation. J Cell Biol 182(1):185-196.
Liu, H., Wang, P., Song, W., and Sun, X. Degradation of regulator of calcineurin 1 (RCAN1) is mediated by both chaperone-mediated autophagy and ubiquitin proteasome pathways, (2009) FASEB J 23, 3383-3392.
Luo W, et al. (2007) Roles of heat-shock protein 90 in maintaining and facilitating the neurodegenerative phenotype in tauopathies. Proc Natl Acad Sci U S A 104(22):9511-9516.
Marzec, M., Eletto, D. & Argon, Y. GRP94: An HSP90-like protein specialized for protein folding and quality control in the endoplasmic reticulum. Biochemica et Biophysica Acta, 1823:74-787, (2012).

(Continued)

*Primary Examiner* — Joseph Kosack
*Assistant Examiner* — Amanda L Aguirre
(74) *Attorney, Agent, or Firm* — Michele L. Lawson; Smith & Hopen, P.A.

(57) ABSTRACT

A compound and method for treating myocilin glaucoma using a selective Grp94 inhibitor is presented. Clearance of mutant myocilin can be promoted by selectively targeting the endoplasmic reticulum (ER) chaperone Grp94 using siRNA knockdown or small molecule inhibitors. Grp94 contributes to the intracellular accumulation of mutant myocilin. Tailored treatments aimed at disrupting the Grp94/mutant myocilin interaction can be used as a new therapeutic strategy for myocilin glaucoma. The inventors developed a compound having a general backbone structure of geldanamycin (GDA) and radicicol (RDC) in which a more hydrophobic surrogate of the quinone in GDA is linked to the resorcinol in RDC through a cis-amide bioisostere.

2 Claims, 16 Drawing Sheets

(56) References Cited

OTHER PUBLICATIONS

Maynard, J. C. et al. Gp93, the *Drosophila* GRP94 ortholog, is required for gut epithelial homeostasis and nutrient assimilation-coupled growth control. Dev. Biol. 339, 295-306, (2010).

McLaughlin, M. & Vandenbroeck, K. The endoplasmic reticulum protein folding factory and its chaperones: new targets for drug discovery? British Journal of Pharmacology 162, 328-345, (2011).

Melnick, J., Dul, J. L. & Argon, Y. Sequential interaction of the chaperones BiP and GRP94 with immunoglobulin chains in the endoplasmic reticulum. Nature 370, 373-375, (1994).

Meusser B, Hirsch C, Jarosch E, & Sommer T (2005) ERAD: the long road to destruction. Nat Cell Biol 7(8):766-772.

Moorehead, R. A., Sanchez, O. H., Baldwin, R. M. & Khokha, R. Transgenic overexpression of IGF-II induces spontaneous lung tumors: a model for human lung adenocarcinoma. Oncogene 22, 853-857, (2003).

Morales C, Wu S, Yang Y, Hao B, & Li Z (2009) *Drosophila* glycoprotein 93 ortholog of mammalian heat shock protein gp96 (grp94, HSP90b1, HSPC4) and retains disulfide bond-independent chaperone function for TLRs and integrins. J Immunol 183(8):5121-5128.

Morello JP, et al. (2000) Pharmacological chaperones rescue cell-surface expression and function of misfolded V2 vasopressin receptor mutants. J Clin Invest 105(7):887-895.

Muchowski PJ & Wacker JL (2005) Modulation of neurodegeneration by molecular chaperones. Nat Rev Neurosci 6 (1):11-22.

Neckers, L. Hsp90 inhibitors as novel cancer chemotherapeutic agents. Trends Mol. Med. 8(4): S55-S61, (2002).

Neckers L & Workman P (2012) Hsp90 molecular chaperone inhibitors: are we there yet? Clin Cancer Res 18(1):64-76.

Olson, D. L, Burkly, L. C., Leone, D. R., Dolinski, B. M. & Lobb, R. R. Anti-α4 integrin monoclonal antibody inhibits multiple myeloma growth in a murine model. Molecular Cancer Therapeutics 4, 91-99, (2005).

Orwig SD, et al. (2011) Amyloid Fibril Formation by the Glaucoma-Associated Olfactomedin Domain of Myocilin. J Mol Biol, (2012) 421, 242-255.

Ostrovsky, O., Ahmed, N. T. & Argon, Y. The Chaperone Activity of GRP94 Toward Insulin-like Growth Factor II Is Necessary for the Stress Response to Serum Deprivation. Mol. Biol. Cell, 20:1855-1864, (2009).

Ostrovsky, O., Eletto, D., Makarewich, C., Barton, E. R. & Argon, Y. Glucose regulated protein 94 is required for muscle differentiation through its control of the autocrine production of insulin-like growth factors. Biochimica et Biophysica Acta, 1803:333-341, (2010).

Perkumas KM, Hoffman EA, McKay BS, Allingham RR, & Stamer WD (2007) Myocilin-associated exosomes in human ocular samples. Exp Eye Res 84(1):209-212.

Peterson, L. B. & Blagg, B. S. J. To fold or not to fold: modulation and consequences of Hsp90 inhibition. Future Med. Chem.1(2), 267-283, (2009).

Qiu, L., Song, L., Xu, W., Ni, D. & Yu, Y. Molecular cloning and expression of a Toll receptor gene homologue from Zhikong Scallop, *Chlamys farreri.*, Fish Shellfish Immun. 22, 451-466, (2007).

Rajan RS, et al. (2011) Chemical and pharmacological chaperones: application for recombinant protein production and protein folding diseases. Curr Med Chem 18(1):1-15.

Randow, F. & Seed, B. Endoplasmic reticulum chaperone gp96 is required for innate immunity but not cell viability. Nat Cell Biol 3, 891-896, (2001).

Resch ZT & Fautsch MP (2009) Glaucoma-associated myocilin: a better understanding but much more to learn. Exp Eye Res 88(4):704-712.

Ron I & Horowitz M (2005) ER retention and degradation as the molecular basis underlying Gaucher disease heterogeneity. Hum Mol Genet 14(16):2387-2398.

Rousaki A, et al. (2011) Allosteric Drugs: The Interaction of Antitumor Compound MKT-077 with Human Hsp70 Chaperones. J Mol Biol 411(3):614-632.

Rozsa FW, et al. (1998) GLC1A mutations point to regions of potential functional importance on the TIGR/MYOC protein. Mol Vis, 4:20-36.

Saitoh, T. et al. Down-Regulation of Cell Surface Insulin Receptor and Insulin Receptor Substrate-1 Phosphorylation by Inhibitor of 90-kDa Heat-Shock Protein Family: Endoplasmic Reticulum Retention of Monomeric Insulin Receptor Precursor with Calnexin in Adrenal Chromaffin Cells. Molecular Pharmacology 62(4):847-855, (2002).

Santambrogio L & Cuervo AM (2011) Chasing the elusive mammalian microautophagy. Autophagy 7(6):652-654.

Shen, G. & Blagg, B. S. J. Radester, a Novel Inhibitor of the Hsp90 Protein Folding Machinery. Org. Lett., 7(11): 2157-2160, (2005).

Shen, G., Wang, M., Welch, T. R. & Blagg, B. S. J. Design, Synthesis, and Structure Activity Relationships for Chimeric Inhibitors of Hsp90, J. Org. Chem. 71:7618-7631, (2006).

Shepard AR, et al. (2007) Glaucoma-causing myocilin mutants require the Peroxisomal targeting signal-1 receptor (PTS1R) to elevate intraocular pressure. Hum Mol Genet 16(6):609-617.

Soldano, K. L., Jivan, A., Nicchitta, C. V. & Gewirth, D. T. Structure of the N-terminal domain of GRP94. Basis for ligand specificity and regulation. J. Biol. Chem. 278, 48330-48338, (2003).

Sreedhar, A. S., Kalmar, E. & Csermely, P. Hsp90 isoforms: functions, expression and clinical importance. FEBS Lett., 562:11-15, (2004).

Sun, J. et al. Mechanisms of Signal Transduction: Structural and Functional Analyses of the Human Toll-like Receptor 3: Role of Glycosylation, J. Biol. Chem. 281, 11144-11151, (2006).

Supino-Rosin, L., Yoshimura, A., Yarden, Y., Elazar, Z. & Neumann, D. Protein Synthesis Post-Translation Modification and Degradation: Intracellular Retention and Degradation of the Epidermal Growth Factor Receptor, Two Distinct Processes Mediated by Benzoquinone Ansamycins. Journal of Biological Chemistry 275, 21850-21855, (2000).

Abisambra JF, et al. (2010) Phosphorylation dynamics regulate Hsp27-mediated rescue of neuronal plasticity deficits in tau transgenic mice. J Neurosci 30(46):15374-15382.

Adam MF, et al. (1997) Recurrent mutations in a single exon encoding the evolutionarily conserved olfactomedin-homology domain of TIGR in familial open angle glaucoma. Hum Mol Genet 6(12):2091-2097.

Alvarez-Erviti, L.,Rodriguez-Oroz, M. C., Cooper, J. M., Caballero, C., Ferrer, I., Obeso, J. A., and Schapira, A. H. Chaperone-Mediated Autophagy Markers in Parkinson Disease Brains, (2010) Archives of neurology 67(12), 1464-1472.

Alward WL (1998) Medical management of glaucoma. N. Engl. J. Med. 339(18):1298-1307.

Balch WE, Morimoto RI, Dillin A, & Kelly JW (2008) Adapting proteostasis for disease intervention. Science 319 (5865):916-919.

Baldwin, J. J. et al. β-Adrenergic blocking agents with acute antihypertensive activity. J. Med. Chem. 22(6): 687-694, (1979).

Banerji, U. Heat shock protein 90 as a drug target: some like it hot. Clin. Cancer Res. 15, 9-14,(2009).

Basso, A. D. et al. Akt Forms an Intracellular Complex with Heat Shock Protein 90 (Hsp90) and Cdc37 and Is Destabilized by Inhibitors of Hsp90 Function. J. Biol. Chem. 277, 39858-39866, (2002).

Belfiore, A., Pandini, G., Vella, V., Squatrito, S. & Vigneri, R. Insulin/IGF-I hybrid receptors play a major role in IGF-I signaling in thyroid cancer. Biochimie 81, 403-407, (1999).

Benson, J. D. et al. Validating cancer drug targets. Nature 441, 451-456, (2006).

Biamonte, M. A. et al. Heat shock protein 90: inhibitors in clinical trials. J. Med. Chem. 53, 3-17, (2010).

Bishop, S. C., Burlison, J. A. & Blagg, B. S. J. Hsp90: a novel target for the disruption of multiple signaling cascades. Curr. Cancer Drug Tar. 7, 369-388, (2007).

Bjorkoy, G., Lamark, T., Pankiv, S., Overvatn, A., Brech, A., and Johansen, T. (2009) Monitoring Autophagic Degradation of p62/SQSTM1, Methods in enzymology, 452:181-197.

Blagg, B. S. J. & Kerr, T. D. Hsp90 inhibitors: small molecules that transform the Hsp90 protein folding machinery into a catalyst for protein degradation. Med. Res. Rev. 26(3): 310-338, (2006).

(56) References Cited

OTHER PUBLICATIONS

Burns JN, et al. (2010) Rescue of glaucoma-causing mutant myocilin thermal stability by chemical chaperones. ACS Chem Biol 5(5):477-487.

Burns JN, Turnage KC, Walker CA, & Lieberman RL (2011) The stability of myocilin olfactomedin domain variants provides new insight into glaucoma as a protein misfolding disorder. Biochemistry 50(26):5824-5833.

Carbone MA, et al. (2009) Overexpression of myocilin in the *Drosophila* eye activates the unfolded protein response: implications for glaucoma. PLoS One 4(1):e4216.

Carpenter, A. et al. CellProfiler: image analysis software for identifying and quantifying cell phenotypes. Genome Biol.7, R100, (2006).

Chavany, C. et al. p185 Binds to GRP94 in Vivo: Dissociation of the p185/GRP94 Heterocomplex by Benzoquinone Ansamycins Precedes Depletion of p185, Journal of Biological Chemistry 271(9):4974-4977, (1996).

Chen, Y., McMillan-Ward, E., Kong, J., Israels, S. J., and Gibson, S. B. (2008), Oxidative Stress Induces Autophagic Cell Death Independent of Apoptosis in Transformed and Cancer Cells, Cell Death Differ 15, 171-182.

Chiosis, G., Vilenchik, M., Kim, J. & Solit, D. Hsp90: the vulnerable chaperone. Drug Discov. Today 9(20):881-888, (2004).

Clevenger, R. C. & Blagg, B. S. J. Design, Synthesis, and Evaluation of a Radicicol and Geldanamycin Chimera, Radamide. Org. Lett. 6(24): 4459-4462, (2004).

da Rocha Dias, S. et al. Activated B-RAF Is an Hsp90 Client Protein That Is Targeted by the Anticancer Drug 17- Allylamino-17-Demethoxygeldanamycin. Cancer Res. 65, 10686-10691, (2005).

Dickey CA, et al. (2007) The high-affinity HSP9O-CHIP complex recognizes and selectively degrades phosphorylated tau client proteins. J Clin Invest 117(3):648-658.

Dollins, D. E., Immormino, R. M. & Gewirth, D. T. Structure of unliganded GRP94, the ER Hsp90: Basis for nucleotide-induced conformational change. J. Biol. Chem., 280: 30438-30447, (2005).

Dollins, D. E., Warren, J. J., Immormino, R. M. & Gewirth, D. T. Structures of GRP94-nucleotide complexes reveal mechanistic differences between the hsp90 chaperones. Mol. Cell 28, 41-56, (2007).

Dutta, R. & Inouye, M. GHKL, An emergent ATPase/kinase superfamily. Trends Biochem. Sci., 25:24-28, (2000).

Eletto D, Dersh D, & Argon Y (2010) GRP94 in ER quality control and stress responses. Sem in Cell Dev Biol, 21 (5):479-485.

Fan JQ, Ishii S, Asano N, & Suzuki Y (1999) Accelerated transport and maturation of lysosomal alpha-galactosidase A in Fabry lymphoblasts by an enzyme inhibitor. Nat Med 5(1):112-115.

Farinha CM & Amaral MD (2005) Most F508del-CFTR is targeted to degradation at an early folding checkpoint and independently of calnexin. Mol Cell Biol, 25(12):5242-5252.

Fingert JH, et al. (1999) Analysis of myocilin mutations in 1703 glaucoma patients from five different populations. Hum Mol Genet 8(5):899-905.

Garriga P, Liu X, & Khorana HG (1996) Structure and function in rhodopsin: correct folding and misfolding in point mutants at and in proximity to the site of the retinitis pigmentosa mutation Leu-125—>Arg in the transmembrane helix C. Proc Natl Acad Sci U S A , 93(10):4560-4564.

Ge J, Zhuo Y, Guo Y, Ming W, & Yin W (2000) Gene mutation in patients with primary open-angle glaucoma in a pedigree in China. Chin. Med. J., 113(3):195-197.

Gobeil S, Letartre L, & Raymond V (2006) Functional analysis of the glaucoma causing TIGR/myocilin protein: integrity of amino-terminal coiled-coil regions and olfactomedin homology domain is essential for extracellular adhesion and secretion. Exp Eye Res 82(6):1017-1029.

Gong G, Kosoko-Lasaki O, Haynatzki GR, & Wilson MR (2004) Genetic dissection of myocilin glaucoma. Hum. Mol. Genet. 13(1):R91-102.

Gould DB, et al. (2006) Mutant myocilin nonsecretion in vivo is not sufficient to cause glaucoma. Mol Cell Biol, 26 (22):8427-8436.

Grbovic, O. M. et al. V600E B-Raf requires the Hsp90 chaperone for stability and is degraded in response to Hsp90 inhibitors. P. Natl. Acad. Sci. 103(1): 57-62, (2006).

Hadden, M. K. & Blagg, B. S. J. Synthesis and Evaluation of Radamide Analogues, A Chimera of Radicicol and Geldanamycin. J. Org. Chem. 74, 4697-4704, (2009).

Hanahan, D. & Weinberg, R. A. The hallmarks of cancer. Cell 100, 57-70, (2000).

Hanahan, D. & Weinberg, Robert A. Hallmarks of cancer: The next generation. Cell 144, 646-674, (2011).

Hardy KM, Hoffman EA, Gonzalez P, McKay BS, & Stamer WD (2005) Extracellular trafficking of myocilin in human trabecular meshwork cells. The Journal of biological chemistry 280(32):28917-28926.

Hartl, F. U. Molecular chaperones in cellular protein folding. Nature 381, 571-580, (1996).

Hartl, F. U., Bracher, A. & Hayer-Hartl, M. Molecular chaperones in protein folding and proteostasis. Nature 475, 324-332, (2011).

Holzbeierlein, J., Windsperger, A. & Vielhauer, G. Hsp90: A Drug Target? Curr. Oncol. Rep. 12, 95-101,(2010).

Immormino, R. M. et al. Different Poses for Ligand and Chaperone in Inhibitor-Bound Hsp90 and GRP94: Implications for Paralog-Specific Drug Design. J. Mol. Biol. 388, 1033-1042, (2009).

Isaacs, J. S., Xu, W. S. & Neckers, L. Heat shock protein as a molecular target for cancer therapeutics. Cancer Cell 3, 213-217, (2003).

Istomin, A. & Godzik, A. Understanding diversity of human innate immunity receptors: analysis of surface features of leucine-rich repeat domains in NLRs and TLRs. BMC Immunology 10, 48-63 (2009).

Jia Ly, et al. (2009) Correction of the disease phenotype of myocilin-causing glaucoma by a natural osmolyte. Invest Ophthalmol Vis Sci 50(8):3743-3749.

Jinwal UK, et al. (2009) Chemical manipulation of hsp70 ATPase activity regulates tau stability. J Neurosci 29 (39):12079-12088.

Joe MK, et al. (2003) Accumulation of mutant myocilins in ER leads to ER stress and potential cytotoxicity in human trabecular meshwork cells. Biochem Biophys Res Commun 312(3):592-600.

Tabas I & Ron D (2011) Integrating the mechanisms of apoptosis induced by endoplasmic reticulum stress. Nat Cell Biol 13(3):184-190.

Taldone, T., Gozman, A., Maharaj, R. & Chiosis, G. Targeting Hsp90: small-molecule inhibitors and their clinical development. Curr. Opin. Pharmacol. 8, 370-374, (2008).

Tanaka, Y., Guhde, G., Suter, A., Eskelinen, E. L., Hartmann, D., Lullmann-Rauch, R., Janssen, P. M., Blanz, J., von Figura, K., and Saftig, P. (2000) Accumulation of Autophagic vacuoles and cardiomyopathy in LAMP-2-deficient mice, Nature 406, 902-906.

Vogen, S. et al. Protein Structure and folding: Radicicol-sensitive Peptide Binding to the N-terminal Portion of GRP94. J. Biol. Chem., 277:40742-40750, (2002).

Vogiatzi, T., Xilouri, M., Vekrellis, K., and Stefanis, L. (2008) Protein Synthesis and Post-Translational Modification and Degradation: Wild type alpha-synuclein is degraded by chaperone-mediated autophagy and macroautophagy in neuronal cells, The Journal of biological chemistry 283:23542-23556.

Vollrath D & Liu Y (2006) Temperature sensitive secretion of mutant myocilins. Exp Eye Res 82(6):1030-1036.

Wanderling, S. et al. GRP94 Is Essential for Mesoderm Induction and Muscle Development Because It Regulates Insulin-like Growth Factor Secretion. Mol. Biol. Cell 18, 3764-3775, (2007).

Wang L, et al. (2007) Pro370Leu mutant myocilin disturbs the endoplasm reticulum stress response and mitochondrial membrane potential in human trabecular meshwork cells. Mol Vis 13:618-625.

Wang X, et al. (2006) Hsp90 co-chaperone Aha1 downregulation rescues misfolding of CFTR in cystic fibrosis. Cell 127(4):803-815.

Weber, A. N. R., Morse, M. A. & Gay, N. J. Four Nlinked Glycosylation Sites in Human Toll-like Receptor 2 Cooperate to Direct Efficient Biosynthesis and Secretion. J. Biol. Chem. 279, 34589-34594, (2004).

Whitesell, L. & Lindquist, S. L. Hsp90 and the chaperoning of cancer. Nat. Rev. Cancer 5, 761-772, (2005).

(56) References Cited

OTHER PUBLICATIONS

Whitesell, L., Bagatell, R. & Falsey, R. The stress response: implications for the clinical development of Hsp90 inhibitors., Curr. Cancer Drug Tar. 3:349-358, (2003).

Workman, P. & Billy, E. d. Putting the heat on cancer. Nat. Med. 13(12):1415-1417, (2007).

Workman, P. Combinatorial attack on multistep oncogenesis by inhibiting the Hsp90 molecular chaperone. Cancer Lett. 206, 149-157, (2004).

Workman, P., Burrows, F., Neckers, L. & Rosen, N. Drugging the cancer chaperone Hsp90: Combinatorial therapeutic exploitation of oncogene addiction and tumor stress. Ann. NY Acad. Sci. 1113:202-216, (2007).

Yam GH, Gaplovska-Kysela K, Zuber C, & Roth J (2007) Sodium 4-phenylbutyrate acts as a chemical chaperone on misfolded myocilin to rescue cells from endoplasmic reticulum stress and apoptosis. Invest Ophthalmol Vis Sci 48 (4):1683-1690.

Yam GH-F, Gaplovska-Kysela K, Zuber C, & Roth J (2007) Aggregated myocilin induces russell bodies and causes apoptosis: implications for the pathogenesis of myocilin-caused primary open-angle glaucoma. Am. J. Pathol. 170 (1):100-109.

Yang, Y. et al. Heat shock protein gp96 is a master chaperone for toll-like receptors and is important in the innate function of macrophages. Immunity 26, 215-226, (2007).

Ye Y, Meyer HH, & Rapoport TA (2001) The AAA ATPase Cdc48/p97 and its partners transport proteins from the ER into the cytosol. Nature 414:652-656.

Zhang, H. & Burrows, F. Targeting multiple signal transduction pathways through inhibition of Hsp90. J. Mol. Med. 82: 488-499, (2004).

Zhou Z & Vollrath D (1999) A cellular assay distinguishes normal and mutant TIGR/myocilin protein. Hum Mol Genet ,8 (12):2221-2228.

Zode GS, et al. (2011) Reduction of ER stress via a chemical chaperone prevents disease phenotypes in a mouse model of primary open angle glaucoma. J Clin Invest 121(9):3542-3553.

Zode GS, et al. (2012) Topical ocular sodium 4-phenylbutyrate rescues glaucoma in a myocilin mouse model of primary open-angle glaucoma. Invest. Ophthalmol. Vis. Sci. 53(3):1557-1565.

Zuany-Amorim, C., Hastewell, J. & Walker, C. Toll-like receptors as potential therapeutic targets for multiple diseases. Nat Rev Drug Discov, 1: 797-807, (2002).

Immormino, R. M. et al. Ligand-induced conformational shift in the N-terminal domain of GRP94, an Hsp90 chaperone. J. Biol. Chem., 279:46162-46171, (2004).

McLaughlin, M., Alloza, I. & Vandenbroeck, K. Different chaperone usage by IL-12 and IL-23 during their assembly reveals novel targets for intervention with cytokine secretion in neuroinflammation. Neuroimmunol. 203, p. 268, (2008).

\* cited by examiner

Geldanamycin (GDA)    Radicicol (RDC)    Radamide (RDA)

Figure 17

COMPOSITIONS AND METHODS OF TREATMENT FOR MYOCILIN GLAUCOMA BY SELECTIVELY INHIBITING GRP94

CROSS REFERENCE TO RELATED APPLICATIONS

This application is a nonprovisional of and claims priority to U.S. Provisional Patent Application No. 61/727,561, entitled "GRP94 Triage of Mutant Myocilin Through ERAD Subverts a More Efficient Autotrophic Clearance Mechanism", filed Nov. 16, 2012, the entire contents of which is herein incorporated into this disclosure.

FIELD OF INVENTION

This invention relates to treatment of glaucoma. Specifically, the invention provides a method of treating myocilin glaucoma and related compositions by selectively inhibiting Grp94.

BACKGROUND OF THE INVENTION

Myocilin is the gene product most closely linked to early-onset, inherited primary open angle glaucoma (POAG), accounting for more than 10% of juvenile and 5% of adult-onset disease. (Kwon Y H, Fingert J H, Kuehn M H, & Alward W L (2009) Primary open-angle glaucoma. *N. Engl. J. Med.* 360(11):1113-1124; Fingert J H, et al. (1999) Analysis of myocilin mutations in 1703 glaucoma patients from five different populations. *Hum Mol Genet* 8(5):899-905) Even though it is expressed throughout the body, myocilin only appears to cause disease as part of its role in the trabecular meshwork (TM), an extracellular matrix in the anterior segment of the eye that controls aqueous humor outflow and is involved in regulating intraocular pressure (IOP). (Resch Z T & Fautsch M P (2009) Glaucoma-associated myocilin: a better understanding but much more to learn. *Exp Eye Res* 88(4):704-712) Dysregulation of fluid flow leads to elevated IOP, a major risk factor for glaucoma. (Alward W L (1998) Medical management of glaucoma. *N. Engl. J. Med.* 339(18): 1298-1307) Amino acid altering mutations in the gene encoding myocilin lead to sequestration and accumulation of mutant myocilin, particularly in the ER of TM cells with toxic consequences of cell stress and death that lead to a compromised TM and a hastening of glaucoma phenotypes. (Joe M K, et al. (2003) Accumulation of mutant myocilins in ER leads to ER stress and potential cytotoxicity in human trabecular meshwork cells. *Biochem Biophys Res Commun* 312(3): 592-600; Liu Y & Vollrath D (2004) Reversal of mutant myocilin non-secretion and cell killing: implications for glaucoma. *Hum Mol Genet* 13(11):1193-1204; Yam G H-F, Gaplovska-Kysela K, Zuber C, & Roth J (2007) Aggregated myocilin induces russell bodies and causes apoptosis: implications for the pathogenesis of myocilin-caused primary open-angle glaucoma. *Am. J. Pathol.* 170(1):100-109; Gobeil S, Letartre L, & Raymond V (2006) Functional analysis of the glaucoma causing TIGR/myocilin protein: integrity of amino-terminal coiled-coil regions and olfactomedin homology domain is essential for extracellular adhesion and secretion. *Exp Eye Res* 82(6):1017-1029; Vollrath D & Liu Y (2006) Temperature sensitive secretion of mutant myocilins. *Exp Eye Res* 82(6):1030-1036; Wang L, et al. (2007) Pro370Leu mutant myocilin disturbs the endoplasm reticulum stress response and mitochondrial membrane potential in human trabecular meshwork cells. *Mol Vis* 13:618-625)

Interestingly, over 70 mutations in myocilin, clustered in its C-terminal ~30 kDa olfactomedin (OLF) domain, have been documented, with differing severity in terms of age of onset, cellular toxicity, and extent of thermal destabilization of the OLF domain. (Gobeil S, Letartre L, & Raymond V (2006) Functional analysis of the glaucoma causing TIGR/myocilin protein: integrity of amino-terminal coiled-coil regions and olfactomedin homology domain is essential for extracellular adhesion and secretion. *Exp Eye Res* 82(6): 1017-1029; Vollrath D & Liu Y (2006) Temperature sensitive secretion of mutant myocilins. *Exp Eye Res* 82(6):1030-1036; Gong G, Kosoko-Lasaki O, Haynatzki G R, & Wilson M R (2004) Genetic dissection of myocilin glaucoma. *Hum. Mol. Genet.* 13:R91-102; Burns J N, et al. (2010) Rescue of glaucoma-causing mutant myocilin thermal stability by chemical chaperones. *ACS Chem Biol* 5(5):477-487; Burns J N, Turnage K C, Walker C A, & Lieberman R L (2011) The stability of myocilin olfactomedin domain variants provides new insight into glaucoma as a protein misfolding disorder. *Biochemistry* 50(26):5824-5833)

Importantly, pathogenesis is a gain-of-toxic-function, as myocilin knockout mice, and individuals harboring premature stop codons that prevent myocilin translation, do not develop glaucoma. (Gould D B, et al. (2006) Mutant myocilin nonsecretion in vivo is not sufficient to cause glaucoma. *Mol Cell Biol* 26(22):8427-8436; Lam D S, et al. (2000) Truncations in the TIGR gene in individuals with and without primary open-angle glaucoma. *Invest Ophthalmol Vis Sci* 41(6): 1386-1391) The nature of the aggregate and its toxicity has not been unambiguously identified, but the Unfolded Protein Response is upregulated in cells expressing high levels of wild-type myocilin and ER stress response genes are upregulated both in cells and in mice expressing mutant myocilin. (Joe M K, et al. (2003) Accumulation of mutant myocilins in ER leads to ER stress and potential cytotoxicity in human trabecular meshwork cells. *Biochem Biophys Res Commun* 312(3):592-600; Carbone M A, et al. (2009) Overexpression of myocilin in the *Drosophila* eye activates the unfolded protein response: implications for glaucoma. *PLoS One* 4(1): e4216; Zode G S, et al. (2011) Reduction of ER stress via a chemical chaperone prevents disease phenotypes in a mouse model of primary open angle glaucoma. *J Clin Invest* 121(9): 3542-3553)

Mutant myocilin also readily forms a detergent-insoluble species consisting of amyloid fibrils, a specific misfolded species that is recalcitrant to disaggregation, in vitro and in a cellular model. (Zhou Z & Vollrath D (1999) A cellular assay distinguishes normal and mutant TIGR/myocilin protein. *Hum Mol Genet* 8(12):2221-2228; Orwig S D, et al. (2011) Amyloid Fibril Formation by the Glaucoma-Associated Olfactomedin Domain of Myocilin. *J Mol Biol*)

In spite of the interest in developing therapeutic routes to mitigate myocilin aggregation and toxicity, primarily by promoting its secretion, it is not understood why myocilin, unlike other mutant proteins, is not efficiently cleared by ER-associated degradation (ERAD). (Liu Y & Vollrath D (2004) Reversal of mutant myocilin non-secretion and cell killing: implications for glaucoma. *Hum Mol Genet* 13(11):1193-1204; Burns J N, et al. (2010) Rescue of glaucoma-causing mutant myocilin thermal stability by chemical chaperones. *ACS Chem Biol* 5(5):477-487; Zode G S, et al. (2011) Reduction of ER stress via a chemical chaperone prevents disease phenotypes in a mouse model of primary open angle glaucoma. *J Clin Invest* 121(9):3542-3553; Jia L Y, et al. (2009) Correction of the disease phenotype of myocilin-causing glaucoma by a natural osmolyte. *Invest Ophthalmol Vis Sci* 50(8):3743-3749; Yam G H, Gaplovska-Kysela K, Zuber C, & Roth J (2007) Sodium 4-phenylbutyrate acts as a chemical chaperone on misfolded myocilin to rescue cells from endoplasmic reticulum stress and apoptosis. *Invest Ophthalmol Vis Sci* 48(4):1683-1690; Zode G S, et al. (2012) Topical ocular sodium 4-phenylbutyrate rescues glaucoma in a myocilin mouse model of primary open-angle glaucoma. *Invest. Ophthalmol. Vis. Sci.* 53(3):1557-1565) Misfolded proteins are typically efficiently ubiquitinated in the ER and retro-translocated to the cytosol for proteasomal degradation, a mechanism that appears to be challenged in the case of mutant myocilin.

Chaperone 4 proteins within the ER, primarily ATPases Grp94 (an Hsp90 family member) and Grp78 (an Hsp70 member, also called BiP), are essential for triage decisions about protein fate. (Meusser B, Hirsch C, Jarosch E, & Sommer T (2005) ERAD: the long road to destruction. *Nat Cell Biol* 7(8):766-772) The exact order in which ER clients are processed by chaperones is unknown; however Grp94 seems to be much more selective for a distinct client sub-set. (Eletto D, Dersh D, & Argon Y (2010) GRP94 in ER quality control and stress responses. *Semin Cell Dev Biol* 21(5):479-485) Indeed, Grp94 and Grp78 have been shown to co-localize with mutant myocilin, but the significance of this co-localization has remained elusive. ERAD-related loss of function due to inherited mutation is associated with myriad diseases such as cystic fibrosis and Gaucher disease, among many others. (Joe M K, et al. (2003) Accumulation of mutant myocilins in ER leads to ER stress and potential cytotoxicity in human trabecular meshwork cells. *Biochem Biophys Res Commun* 312(3):592-600; Liu Y & Vollrath D (2004) Reversal of mutant myocilin non-secretion and cell killing: implications for glaucoma. *Hum Mol Genet* 13(11):1193-1204; Zode G S, et al. (2011) Reduction of ER stress via a chemical chaperone prevents disease phenotypes in a mouse model of primary open angle glaucoma. *J Clin Invest* 121(9):3542-3553; Yam G H, Gaplovska-Kysela K, Zuber C, & Roth J (2007) Sodium 4-phenylbutyrate acts as a chemical chaperone on misfolded myocilin to rescue cells from endoplasmic reticulum stress and apoptosis. *Invest Ophthalmol Vis Sci* 48(4):1683-1690; Farinha C M & Amaral M D (2005) Most F508del-CFTR is targeted to degradation at an early folding checkpoint and independently of calnexin. *Mol Cell Biol* 25(12):5242-5252; Ron I & Horowitz M (2005) ER retention and degradation as the molecular basis underlying Gaucher disease heterogeneity. *Hum Mol Genet* 14(16):2387-2398) A better understanding of mutant myocilin ER retention could lead to corrective measures that would reduce its accumulation through manipulation of the ER quality control system.

The hereditary form of open angle glaucoma is linked to missense mutations in the MYOC gene. Mutant myocilin misfolding and aggregation in trabecular meshwork cells causes a toxic gain-of-function, namely, cell death, which hastens an increase in intraocular pressure, a primary risk factor for glaucoma. Since the absence of myocilin has no obvious consequence in humans or mice, the inventors speculated that developing ways to deplete aberrant myocilin could be clinically relevant for glaucoma.

SUMMARY OF INVENTION

The inventors have found that clearance of mutant myocilin can be promoted by selectively targeting the endoplasmic reticulum (ER) chaperone Grp94 using siRNA knockdown or small molecule inhibitors. Grp94 selectively recognized mutant myocilin, while wildtype myocilin had no detectable interaction with Grp94. Whereas Grp94 ineffectively attempted to remove mutant myocilin via ER-associated degradation, depleting Grp94 lead to activation of a non-proteasomal alternative pathway for mutant myocilin clearance. Taken together, these findings demonstrate for the first time that Grp94 contributes to the intracellular accumulation of mutant myocilin. Tailored treatments aimed at disrupting the Grp94/mutant myocilin interaction can be developed as a new therapeutic strategy for myocilin glaucoma.

In line with these findings, the inventors also developed inhibitors of Grp94 which can be used to treat myocilin glaucoma. These inhibitors have a general backbone structure of geldanamycin (GDA) and radicicol (RDC) in which a more hydrophobic surrogate of the quinone in GDA is linked to the resorcinol in RDC through a cis-amide bioisostere. The inhibitor should contain 1) A resorcinol ring to ensure N-terminal inhibition and correct orientation within in the ATP-binding pocket, 2) a predisposed cis-amide conformation that projected the phenyl appendage toward the unique Grp94 binding pocket, and 3) a hydrophobic, π-rich surrogate for the quinone of GDA. The cis-amide bioisostere may be imidazole.

In an embodiment, the compound for inhibiting Grp94 has the structure of formula (II) as shown below:

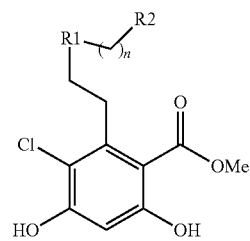

wherein R1 is a cis-amide bioisostere;
wherein R2 is hydrophobic, π-rich moiety; and
wherein n is an integer from 0 to 5.

With regard to formula (II) above, R1 may be selected from the group consisting of cis-olefins, carbocycles and heterocycles. In some embodiments, R1 may be imidazole. R2 may be an aromatic ring such as a phenyl.

BRIEF DESCRIPTION OF THE DRAWINGS

For a fuller understanding of the invention, reference should be made to the following detailed description, taken in connection with the accompanying drawings, in which.

and then treated with increasing concentration of compound 2 for 24 h. prior to staining (blue=DAPI, 60×, air objective, (D); and dose-response curve for Toll-trafficking inhibition of compound 2(E).

Figure 5:
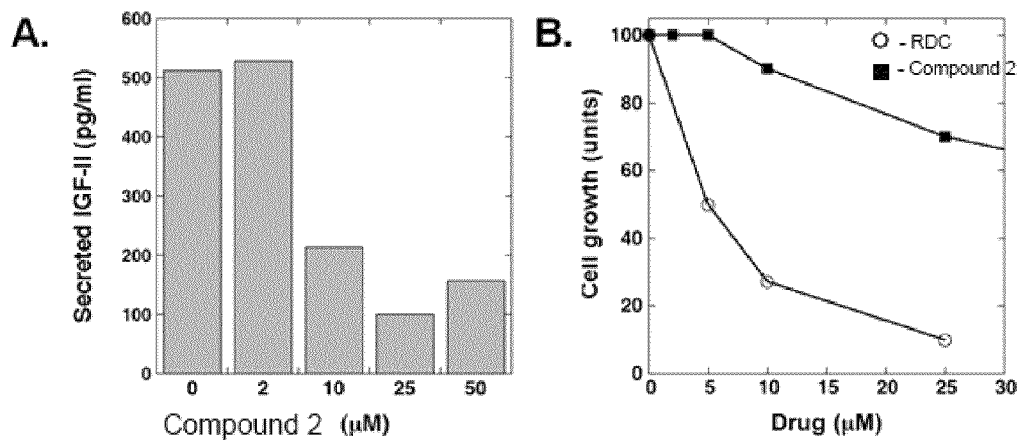

FIGS. 5A-B are a series of graphs depicting inhibition of IFG-II secretion by Compound 2. (A) C2C12 cells were induced to differentiate by serum-starvation in the presence of the indicated concentrations of Compound 2. Supernatants were collected 48 h. later and IFG-II levels measured by ELISA. Drug, concentration range of Compound 2. (B) Toxicity of compound 2(■) and RDC (●) against C2C12 cells. The viability of cells treated as in A was measured at each of the indicated concentrations by the XTT assay.

Figure 6:
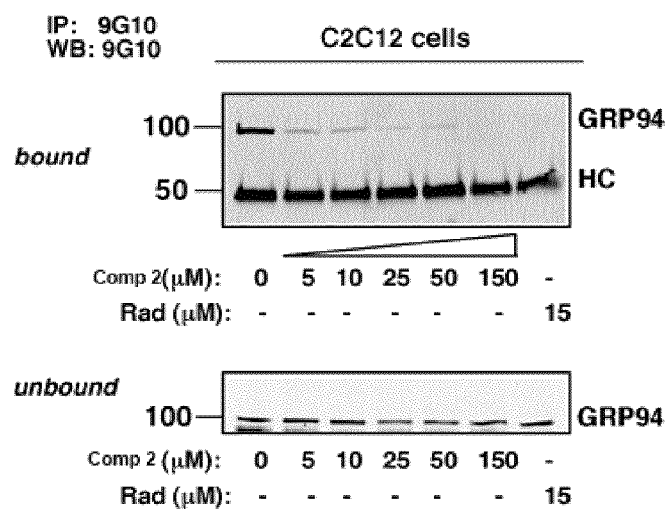

FIG. 6 is an image depicting C2C12 cells were treated with the indicated concentrations of 2 or RDC overnight and cell lysates were immunoprecipitated with the conformation-specific antibody 9G10 and subsequently were immunoblotted for Grp94; lower panel, immunoblot of whole cell lysates with 9G10; HC=heavy chain; N=3.

FIGS. 7A-D are a series of images depicting western blot analysis of HEK293 cell lysates (7.5 µg total protein) after treatment with indicated concentration of compound 2 (µM) for 24 hr. GDA, a known pan-Hsp90 inhibitor is shown as a positive control (500 nM), while actin is shown as a negative, loading control (A); Lysates of HeLa cells stably expressing either scramble shRNA (shCTRL) or GRP94-targeting shRNA (shGRP94) were analyzed by immunoblotting. GRP94 and BiP were detected by the anti-KDEL antibody. *, an unknown KDEL-containing band. 14-3-3 served as loading control (B); HeLa cells as in B) were exposed for 48 hrs at the indicated concentration of compound 2 (C) or RDC (D). Cell survival was measured by XTT assay (n=4).

Figure 8:
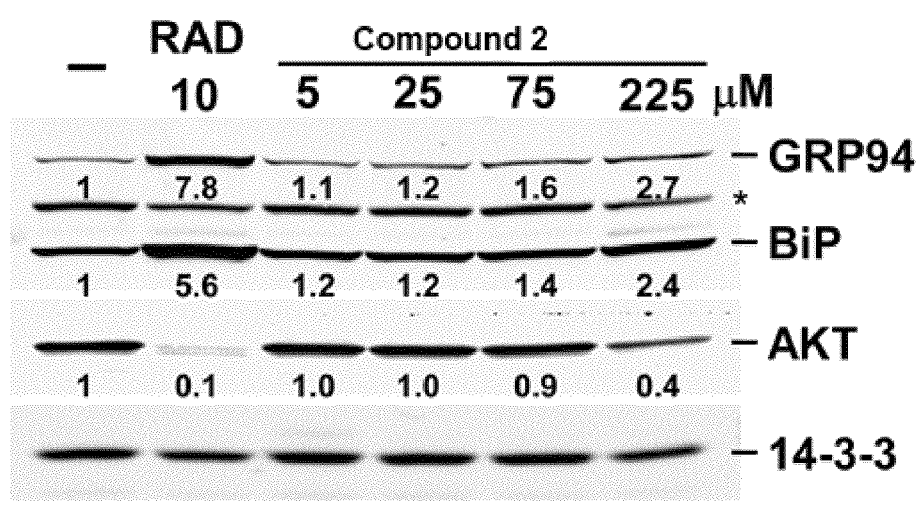

FIG. 8 is an image depicting induction of BiP Expression by treatment with Compound 2. NIH-3T3 cells were treated with 25 µM of 17-AAG (AAG), 10 µM of RDC or 0-50 µM of 2. After 18 hrs cells were harvested for SDS-PAGE and analyzed by immunoblotting. Grp94, BiP and PDIA6 were detected with the monoclonal anti-KDEL antibody, AKT by rabbit anti-serum. 14-3-3 served as loading control. Numbers below BiP, Grp94, and AKT bands are the relative expression levels, determined by densitometry.

FIGS. 9A-H are images depicting effect of Compound 2 on *drosophila* larval growth.

Figure 10:
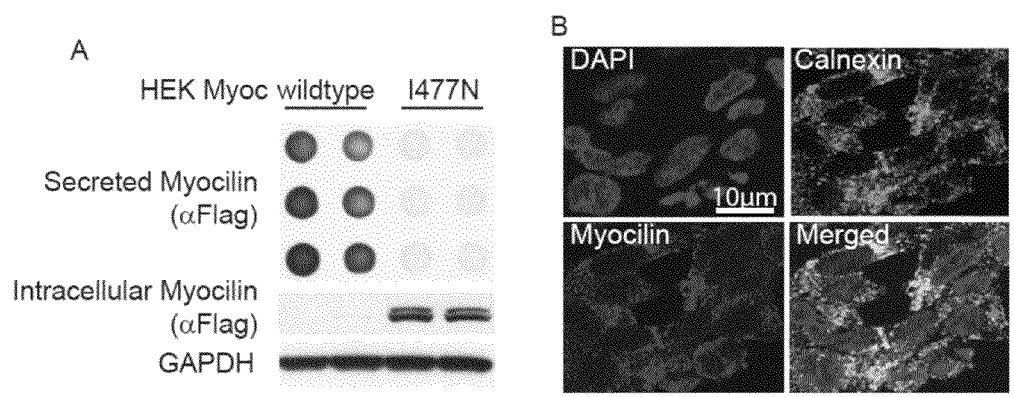
Figure 11:
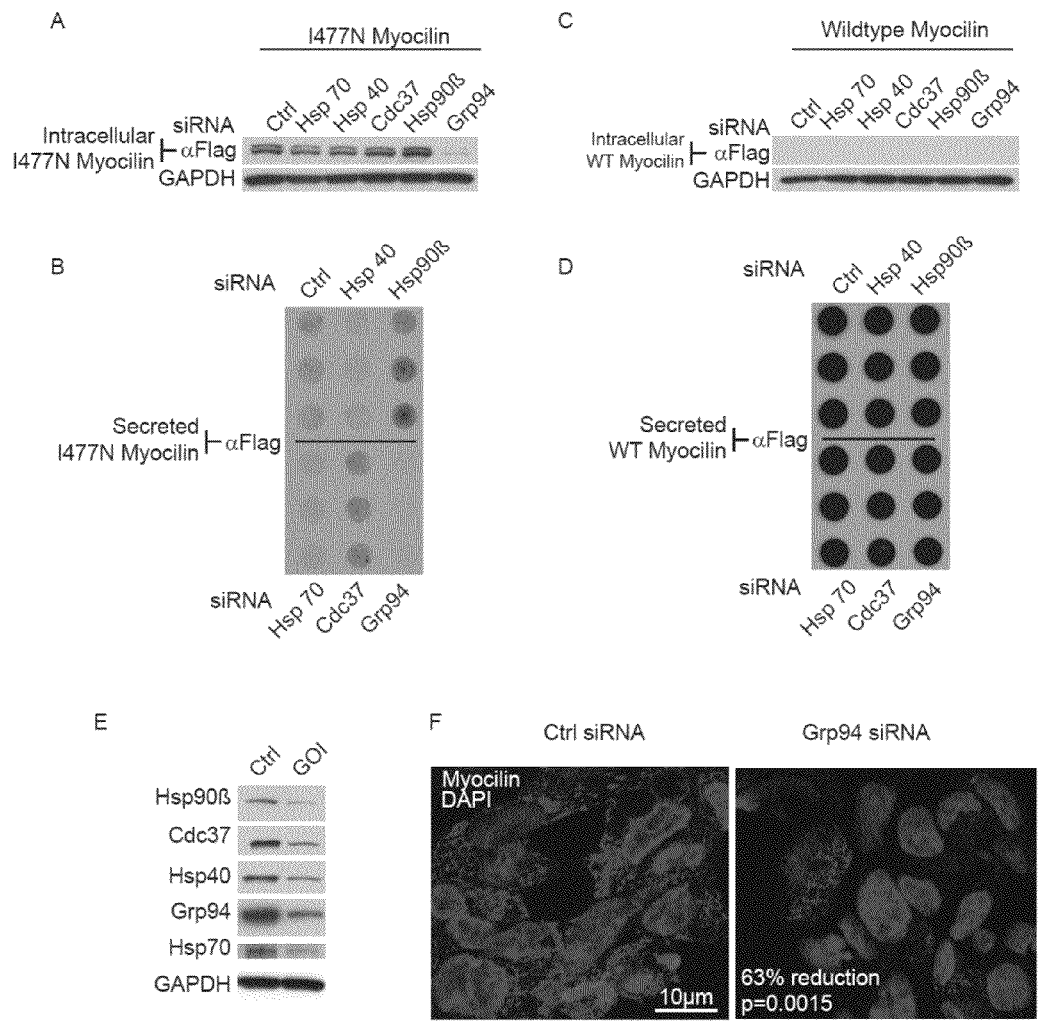

FIGS. 10A-B are a series of images depicting validation of inducible cell model. HEK cells stably over-expressing tetracycline-regulatable Flag-tagged wildtype (iWT) and I477N mutant (iI477N) myocilin were generated as previously described. (A) Dot blot analysis of cell culture media and Western blot of lysates retrieved from both cell lines 96 hours following tetracycline administration. (B) Immunofluorescent co-localization imaging for myocilin (anti-Flag) and the ER marker calnexin of HEK iI477N cells conditionally shows co-localization of myocilin with the ER.

FIGS. 11A-F are a series of images depicting siRNA-mediated knockdown of Grp94 regulates the levels of I477N, but not wildtype, myocilin. Western blot analysis of HEK cells conditionally over-expressing I477N myocilin (iI477N) (A) or wildtype myocilin (iWT) (C) shows the intracellular levels of myocilin after the siRNA mediated knockdown of Hsp70, Hsp40, Cdc37, Hsp90β, and Grp94 using an anti-Flag antibody. Dot blot of media from HEK iI477N (B) or iWT (D) cells shows the levels of secreted myocilin after the siRNA mediated knockdown of Hsp70, Hsp40, Cdc37, Hsp90β, and Grp94 using an anti-Flag antibody. (E) Western blot analysis of cell lysates from HEK cells transfected with indicated siRNAs using respective antibodies. Following transfection, cultures were maintained for 72 hours to visualize optimal knockdown. GOI indicates gene of interest. (F) Confocal immunofluorescence microscopy of myocilin (red) in HEK iI477N cells following control or Grp94 siRNA transfection. DAPI is shown in blue. Quantitation of myocilin intensity after normalization to DAPI stain showed a 63% reduction in I477N myocilin following Grp94 knockdown. Scale bar=10 µm.

Figure 12:
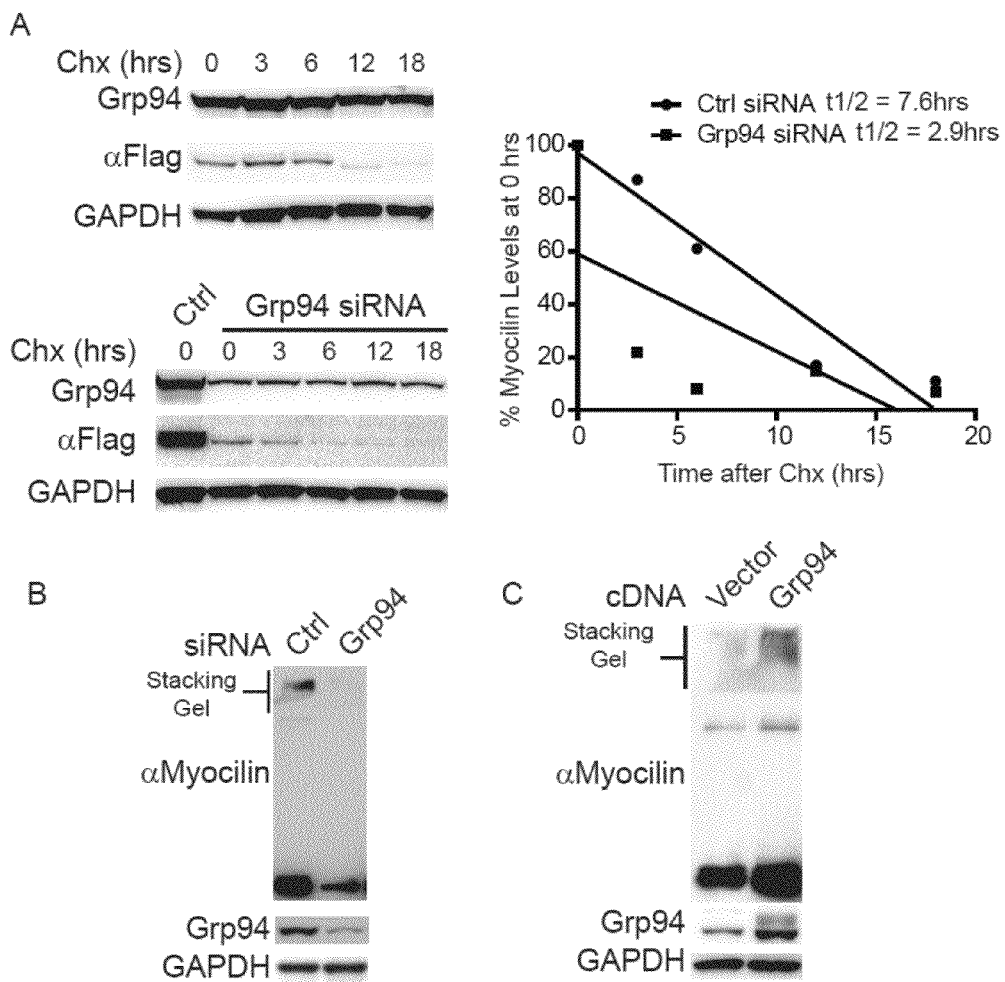

FIGS. 12A-C are a series of images depicting Grp94 preserves mutant myocilin. (A) Western blot analysis of iI477N cell lysates transfected with ctrl siRNA or Grp94 siRNA, treated with 50 µM cycloheximide and harvested at the indicated time points. Half-life of I477N myocilin (t1/2) transfected with control siRNA was determined to be 7.6 hrs. Half-Life of I477N Myocilin transfected with GRP94 siRNA was 2.9 hrs. (B) Western blot of HEK iI477N cell lysates transfected with Ctrl siRNA or Grp94 siRNA. Insoluble myocilin is shown in the stacking gel. Anti-myocilin antibody was used to confirm specificity of the effect. (C) Western blot of HEK iI477N cell lysates transfected with Vector or Grp94 cDNA. Insoluble myocilin is shown in the stacking gel. Anti-myocilin antibody was used to confirm specificity of the effect.

FIGS. 13A-B are a series of images depicting association of Grp94 with mutant but not wildtype myocilin. (A) Co-IP of Flag-tagged myocilin from HEK iI477N or iWT cells followed by Western blot analysis to detect Grp94, myocilin, and GAPDH. Media from cells shows secretion of wildtype but not I477N myocilin as expected. (B) Co-IP of myocilin from HEK cell lysates transiently over-expressing wildtype (WT) or P370L myocilin followed by Western blot for myocilin, Grp94, and GAPDH. As expected, transient over-expression of WT myocilin results in high levels of intracellular myocilin as well as secreted myocilin. P370L was not secreted to the media.

Figure 14:
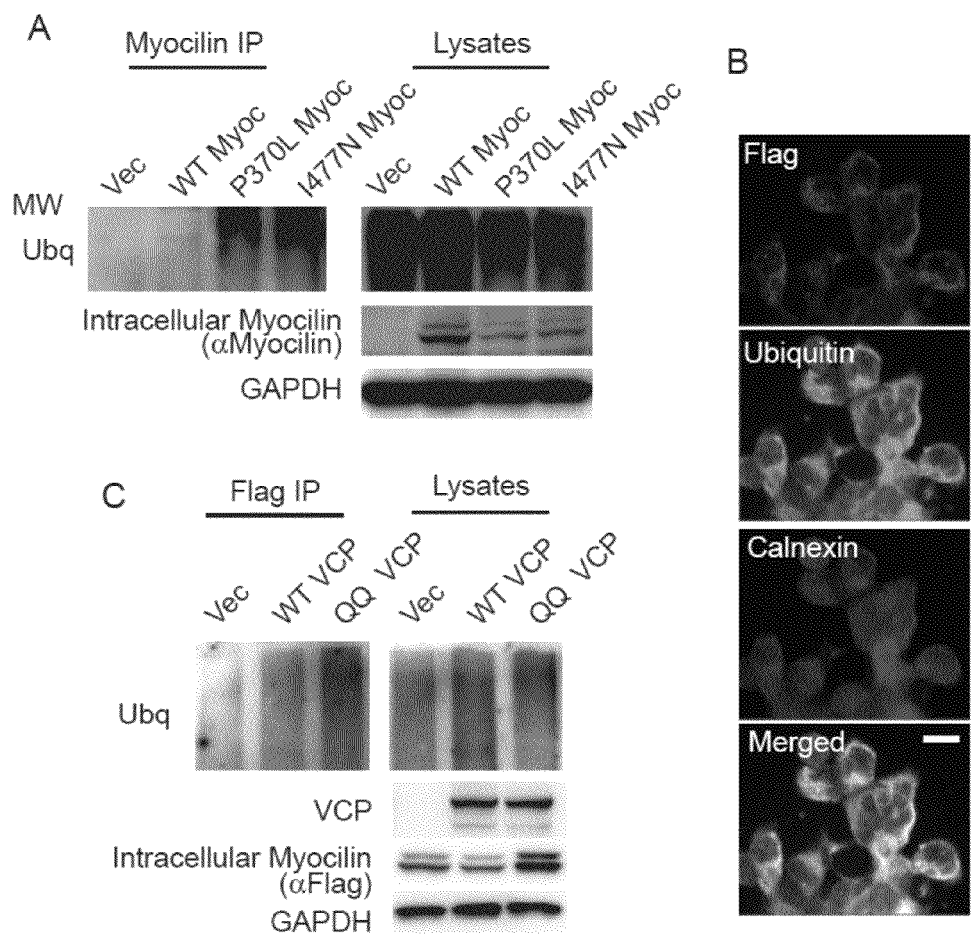

FIGS. 14A-C are a series of images depicting Grp94 sequesters mutant myocilin for ERAD(A) Co-immunopreciptation of myocilin from lysates transiently over-expressing wildtype (WT), P370L and I477N myocilin followed by Western blot for ubiquitin, myocilin and GAPDH. Ubiquitination of myocilin was only observed for the mutant myocilin species. Myocilin was detected with anti-myocilin antibody. MW indicates molecular weight. (B) Immunofluorescent labeling of HEK iI477N cells using anti-Flag to detect myocilin, ubiquitin, and calnexin to indicate ER show that all three probes co-localize (merged). Scale bar=50 µm. (C) Western blot for ubiquitin, myocilin, RGS-His (to detect VCP) and GAPDH of lysates and anti-Flag co-immunopreciptates from HEK iI477N cells transiently transfected with vector (Vec), wildtype VCP (WT VCP) and dominant negative VCP (QQ VCP). Ubiquitination was enhanced in the presence of QQ VCP.

FIGS. 15A-E are a series of images depicting Grp94 knockdown enables efficient autophagic degradation of mutant myocilin (A) Western blot analysis of HEK i477N cell lysates transfected with either control (Ctrl) or Grp94 siRNA and treated with indicated concentrations of the proteasomal inhibitor epoxomicin (Epox). Myocilin was detected with anti-Flag antibody. (B) Confocal immunofluorescent imaging for myocilin with anti-Flag (red) and calnexin from HEK iI477N cells transfected with either control (Ctrl) or Grp94 siRNA. DAPI is shown in blue. Scale bar=40 µm. (C) Western blot of cytosolic and microsome sub-cellular fractions derived from iI477N cells following control (Ctrl) or Grp94 siRNA. Myocilin was detected with anti-myocilin antibody. Western blot analysis of HEK i477N cell lysates transfected with either control (Ctrl) or Grp94 siRNA and either Beclin-1 (D) or Lamp2 (E) siRNAs. Myocilin was detected with anti-myocilin antibody.

FIGS. 16A-E are a series of images depicting inhibition of the Hsp90 chaperone complex reduces the levels of the disease-causing I477N myocilin. Western blot of lysates from HEK iI477N cells treated with the indicated concentrations of the pan Hsp90/Grp94 inhibitors 17-AAG (A) and celastrol (B) for 24 hours. (C) Western blot of lysates from HEK cells conditionally over-expressing I477N myocilin that were treated with 7.5 μM of 17-AAG or vehicle (Veh) and harvested at indicated time points. (D) Dot blot of the cell culture media of HEK iWT cells that were treated with the indicated concentration of 17AAG. (E) Western blot of lysates from HEK iI477N cells and treated with indicated concentrations of a Grp94 selective inhibitor for 24 hours.

Figure 17:
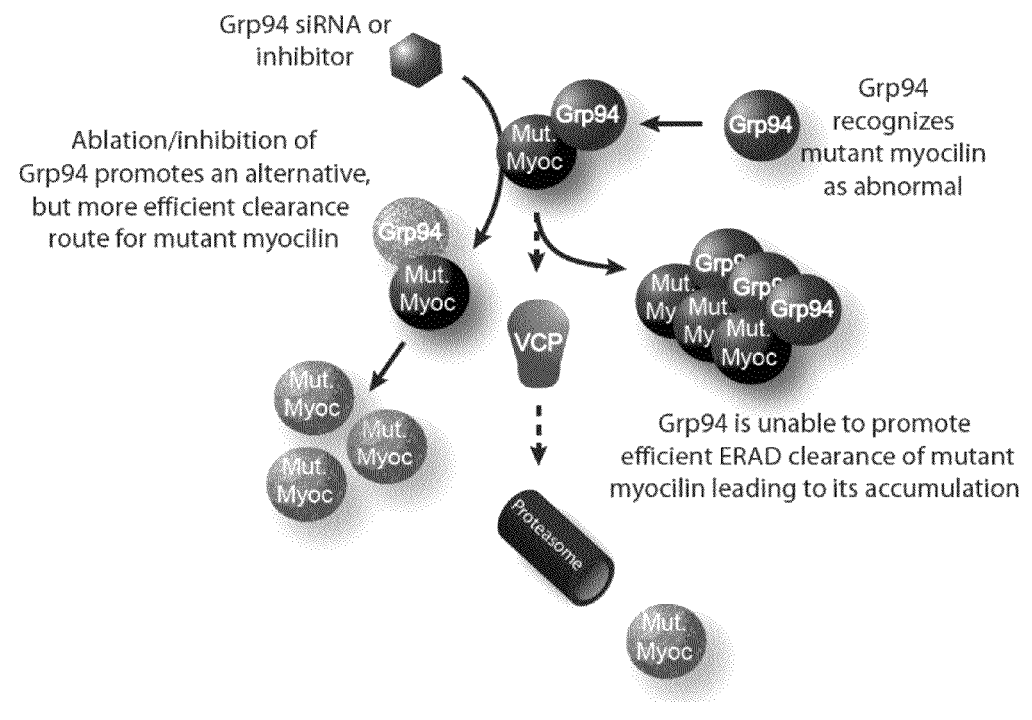

FIG. 17 is an image depicting mutant myocilin becomes a client of Grp94 and is inefficiently processed by ERAD. Schematic showing that mutant myocilin becomes a Grp94 client and is triaged for ERAD. ERAD is not sufficient to prevent mutant myocilin accumulation. Knockdown or inhibition of Grp94 facilitates much more rapid clearance of mutant myocilin species via autophagy.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise. For example, the term "a nanoparticle" includes a plurality of nanoparticles, including mixtures thereof.

"Patient" is used to describe an animal, preferably a human, to whom treatment is administered, including prophylactic treatment with the compositions of the present invention.

The "therapeutically effective amount" for purposes herein is thus determined by such considerations as are known in the art. A therapeutically effective amount of the Grp94 inhibitor is that amount necessary to provide a therapeutically effective result in vivo. The amount of Grp94 inhibitor must be effective to achieve a response, including but not limited to total prevention of (e.g., protection against) and to improved survival rate or more rapid recovery, or improvement or elimination of symptoms associated with eye disorders such as glaucoma, specifically myocilin glaucoma, as well as other mutant myocilin-related disorders, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

"Administration" or "administering" is used to describe the process in which a small molecule inhibitor such as a Grp94 inhibitor of the present invention is delivered to a patient. The composition may be administered in various ways including parenteral (referring to intravenous, intraarterial and other appropriate parenteral routes), intraocular, topically, orally, and percutaneously, among others. Each of these conditions may be readily treated using other administration routes of Grp94 inhibitors to treat a disease or condition.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically or topically administering drugs. These pharmaceutical compositions are desirably in unitary dosage form suitable, preferably, for administration orally, topically, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used in other embodiments of the present invention. Additionally, compounds used in the present invention may be administered in combination with or concurrently with other therapeutics for glaucoma disorders.

The term "cis-olefin" as used herein refers to an unsaturated chemical compound containing at least one carbon-carbon double bond in which each carbon has one substituent each that is on the same side of the bond. The terms "olefin" and "alkene" are used interchangeably herein. The cis-olefins used in the present invention should exhibit a conformational bias for the cis-amide conformation in order to project the hydrophobic aromatic compound into the Grp94 hydrophobic pocket.

The term "carbocyle" as used herein refers to an acyclic organic compound that is both aliphatic and cyclic. The compound may contain one or more all-carbon rings which can be saturated or unsaturated but are not aromatic. Carbocycle compounds may have one or more aliphatic side chains. Examples of carbocycles may include monocyclic cycloalkanes including, but not limited to, cyclopropane, cyclobutane, cyclohexane, cycloheptane and cyclooctane; bicyclic alkanes including, but not limited to, bicycloundecane and decalin; polycyclic alkanes including, but not limited to, cubane, basketane and housane; monocyclic cycloalkenes including, but not limited to, cyclopropene, cyclobutene, cyclopentene, cyclohexene, cycloheptene, and cyclooctene; bicyclic alkenes including, but not limited to, norbornene and norbornadiene. The carbocycles used in the present invention should exhibit a conformational bias for the cis-amide conformation in order to project the hydrophobic aromatic compound into the Grp94 hydrophobic pocket.

The term "heterocycle" as used herein refers to a single and multi-cyclic aromatic or non-aromatic ring systems in which at least one of the ring members is an element other than carbon. Heterocycle compounds may include, but are not limited to, pyridine, pyrimidine, furan, thiopene, pyrrole, isoxazole, isothiozole, pyrazole, oxazole, thiazole, imidazole, oxadiazole, thiadiazole, triazole, pyridazine, pyrimidine, pyrazine, triazine, tetrazine, pyrrolidine, piperidine, piperazine, morpholine, azetidine, tetrahydrophan, tetrahydrofuran, dioxane and the like. The heterocycles used in the present invention should exhibit a conformational bias for the cis-amide conformation in order to project the hydrophobic aromatic compound into the Grp94 hydrophobic pocket.

Heat shock protein 90 (Hsp90) represents a promising therapeutic target for the treatment of cancer and other diseases. Unfortunately, results from clinical trials have been disappointing as off-target effects and toxicities has been observed. These detriments may be a consequence of pan-Hsp90 inhibition, as all clinically evaluated Hsp90 inhibitors simultaneously disrupt all four human Hsp90 isoforms.

Using a structure-based approach, the inventors designed an inhibitor of Grp94, the ER-resident Hsp90. The effects of this compound (Compound 2) on several Grp94 and Hsp90α/β (cytosolic isoforms) clients were investigated. Compound 2 prevented intracellular trafficking of the Toll receptor, inhibited the secretion of IGF-II, affected the conformation of Grp94, and prevented *drosophila* larval growth, all Grp94-dependent processes. In contrast, Compound 2 had no effect on cell viability or cytosolic Hsp90α/β client proteins at similar concentrations. The design, synthesis, and evaluation of Compound 2 are described in Example 1 below.

Molecular chaperones play a critical role in cellular homeostasis by modulating the folding, stabilization, activation, and degradation of protein substrates. (Hartl, F. U. Molecular chaperones in cellular protein folding. Nature 381, 571-580, (1996); Hartl, F. U., Bracher, A. & Hayer-Hartl, M. Molecular chaperones in protein folding and proteostasis. *Nature* 475, 324-332, (2011)). Heat shock proteins (Hsps) represent a class of molecular chaperones that are overexpressed in response to cellular stress, including elevated temperatures. (Whitesell, L., Bagatell, R. & Falsey, R. The stress response: implications for the clinical development of Hsp90 inhibitors. *Curr. Cancer Drug Tar.* 3, 349-358, (2003); Whitesell, L. & Lindquist, S. L. Hsp90 and the chaperoning of cancer. *Nat. Rev. Cancer* 5, 761-772, (2005)). Amongst the various Hsps, the 90 kDa heat shock proteins (Hsp90) are considered promising anti-cancer targets due to the role they play in the maturation of various signaling proteins. (Bishop, S. C., Burlison, J. A. & Blagg, B. S. J. Hsp90: a novel target for the disruption of multiple signaling cascades. *Curr. Cancer Drug Tar.* 7, 369-388, (2007); Blagg, B. S. J. & Kerr, T. D. Hsp90 inhibitors: small molecules that transform the Hsp90 protein folding machinery into a catalyst for protein degradation. *Med. Res. Rev.* 26, 310-338, (2006); Chiosis, G., Vilenchik, M., Kim, J. & Solit, D. Hsp90: the vulnerable chaperone. *Drug Discov. Today* 9, 881-888, (2004)). Hsp90 is both overexpressed and activated in transformed cells, which allows for the attainment of high differential selectivities for Hsp90 inhibitors. (Whitesell, L., Bagatell, R. & Falsey, R. The stress response: implications for the clinical development of Hsp90 inhibitors. *Curr. Cancer Drug Tar.* 3, 349-358, (2003); Whitesell, L. & Lindquist, S. L. Hsp90 and the chaperoning of cancer. *Nat. Rev. Cancer* 5, 761-772, (2005); Zhang, H. & Burrows, F. Targeting multiple signal transduction pathways through inhibition of Hsp90. *J. Mol. Med.* 82, 488-499, (2004)). In addition, Hsp90-dependent substrates are directly associated with all six hallmarks of cancer, and thus, through Hsp90 inhibition, multiple oncogenic pathways are simultaneously disrupted, resulting in a combinatorial attack on cancer. (Zhang, H. & Burrows, F. Targeting multiple signal transduction pathways through inhibition of Hsp90. *J. Mol. Med.* 82, 488-499, (2004); Hanahan, D. & Weinberg, R. A. The hallmarks of cancer. *Cell* 100, 57-70, (2000) Hanahan, D. & Weinberg, Robert A. Hallmarks of cancer: The next generation. *Cell* 144, 646-674, (2011); Workman, P. Combinatorial attack on multistep oncogenesis by inhibiting the Hsp90 molecular chaperone. *Cancer Lett.* 206, 149-157, (2004); Workman, P., Burrows, F., Neckers, L. & Rosen, N. Drugging the cancer chaperone Hsp90: Combinatorial therapeutic exploitation of oncogene addiction and tumor stress. *Ann. NY Acad. Sci.* 1113, 202-216, (2007)).

Figure 1:
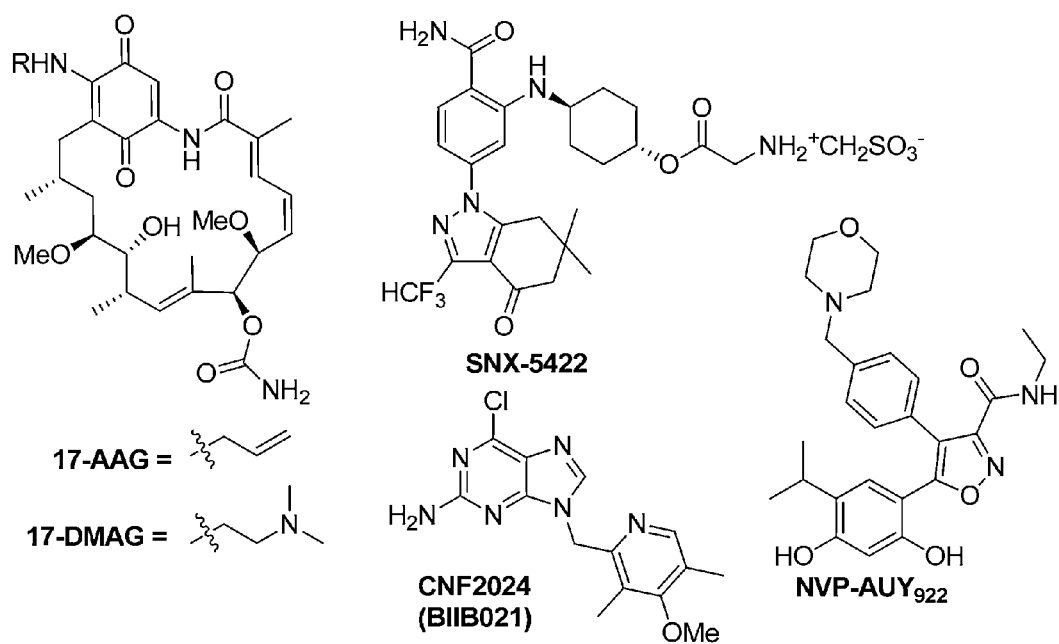
FIG. 1 is an image depicting Hsp90 inhibitors previously or currently under clinical evaluation.

Hsp90 contains an atypical nucleotide binding pocket, which allows for the development of selective inhibitors. (Dutta, R. & Inouye, M. GHKL, An emergent ATPase/kinase superfamily. *Trends Biochem. Sci.* 25, 24-28, (2000)). Several of these Hsp90 N-terminal inhibitors have progressed into clinical trials (FIG. 1), however cardiovascular, ocular, and/or hepatotoxicities have been observed. (Biamonte, M. A. et al. Heat shock protein 90: inhibitors in clinical trials. *J. Med. Chem.* 53, 3-17, (2010); Holzbeierlein, J., Windsperger, A. & Vielhauer, G. Hsp90: A Drug Target? *Curr. Oncol. Rep.* 12, 95-101, (2010); Kim, Y. S. et al. Update on Hsp90 inhibitors in clinical trial. *Curr. Top. Med. Chem.* 9, 1479-1492, (2009)).

Pan-Hsp90 inhibition is likely the cause for these effects, as clinical inhibitors target all four human isoforms; Hsp90α, Hsp90β, Trap1 and Grp94. Hsp90α (inducible) and Hsp90β (constitutively active) are the cytosolic isoforms, whereas tumor necrosis factor receptor associated protein (TRAP1) is localized to the mitochondria, and glucose-regulated protein, Grp94, resides in the endoplasmic reticulum. (Sreedhar, A. S., Kalmar, E. & Csermely, P. Hsp90 isoforms: functions, expression and clinical importance. *FEBS Lett.* 562, 11-15, (2004)). Little is known about the client protein selectivity manifested by each of the four isoforms, and this gap in understanding may underlie the toxicity concerns that have arisen in clinical trials. Despite the clinical significance of Hsp90 inhibition, little investigation towards the development of isoform-selective inhibitors has been pursued to delineate isoform-dependent substrates, or as an opportunity to reduce the side effects that result from pan-inhibition.

Unlike the cytosolic chaperones, Hsp90α and Hsp90β, which have been well-studied, little is known about TRAP1 and Grp94. At present, no isoform specific clients have been described for TRAP-1, In fact, neither the crystal nor the solution structure has been solved. In contrast, Grp94 co-crystal structures have recently been determined, and demonstrate this isoform to exhibit a unique secondary binding pocket that may provide an opportunity to develop isoform-selective inhibitors. (Dollins, D. E., Immormino, R. M. & Gewirth, D. T. Structure of unliganded GRP94, the ER Hsp90: Basis for nucleotide-induced conformational change. *J. Biol. Chem.* 280, 30438-30447, (2005); Dollins, D. E., Warren, J. J., Immormino, R. M. & Gewirth, D. T. Structures of GRP94-nucleotide complexes reveal mechanistic differences between the hsp90 chaperones. *Mol. Cell* 28, 41-56, (2007); Immormino, R. M. et al. Ligand-induced conformational shift in the N-terminal domain of GRP94, an Hsp90 chaperone. *J. Biol. Chem.* 279, 46162-46171, (2004); Immormino, R. M. et al. Different Poses for Ligand and Chaperone in Inhibitor-Bound Hsp90 and GRP94: Implications for Paralog-Specific Drug Design. *J. Mol. Biol.* 388, 1033-1042, (2009); Krukenberg, K. A., Bottcher, U. M., Southworth, D. R. & Agard, D. A. Grp94, the endoplasmic reticulum Hsp90, has a similar solution conformation to cytosolic Hsp90 in the absence of nucleotide. *Protein Sci.* 18, 1815-1827, (2009); Krukenberg, K. A., Southworth, D. R., Street, T. O. & Agard, D. A. pH-dependent conformational changes in bacterial Hsp90 reveal a Grp94-like conformation at pH 6 that is highly active in suppression of citrate synthase aggregation. *J. Mol. Biol.* 390, 278-291, (2009); Soldano, K.

L., Evan, A., Nicchitta, C. V. & Gewirth, D. T. Structure of the N-terminal domain of GRP94. Basis for ligand specificity and regulation. *J. Biol. Chem.* 278, 48330-48338, (2003)). Unlike TRAP-1, several substrates dependent upon Grp94 have been identified and include Toll-like receptors (TLR1, TLR2, TLR4 and TLR9), integrins (CD11a, CD18, CD49d, α4, β7, αL and β2), IGF-I and -II and immunoglobulins. (Marzec, M., Eletto, D. & Argon, Y. GRP94: An HSP90-like protein specialized for protein folding and quality control in the endoplasmic reticulum. *BBA—Mol. Cell Res.* 1823, 774-787, (2012); Maynard, J. C. et al. Gp93, the *Drosophila* GRP94 ortholog, is required for gut epithelial homeostasis and nutrient assimilation-coupled growth control. *Dev. Biol.* 339, 295-306, (2010); McLaughlin, M. & Vandenbroeck, K. The endoplasmic reticulum protein folding factory and its chaperones: new targets for drug discovery? *Brit. J. Pharmacol.* 162, 328-345, (2011); Wanderling, S. et al. GRP94 Is Essential for Mesoderm Induction and Muscle Development Because It Regulates Insulin-like Growth Factor Secretion. *Mol. Biol. Cell* 18, 3764-3775, (2007); MvLaughlin, M., Alloza, I. & Vandenbroeck, K. Different chaperone usage by IL-12 and IL-23 during their assembly reveals novel targets for intervention with cytokine secretion in neuroinflammation. *Neuroimmunol.* 203, 268, (2008); Olson, D. L., Burkly, L. C., Leone, D. R., Dolinski, B. M. & Lobb, R. R. Anti-α4 integrin monoclonal antibody inhibits multiple myeloma growth in a murine model. *Molecular Cancer Therapeutics* 4, 91-99, (2005); Ostrovsky, O., Eletto, D., Makarewich, C., Barton, E. R. & Argon, Y. Glucose regulated protein 94 is required for muscle differentiation through its control of the autocrine production of insulin-like growth factors. *Biochimica et Biophysica Acta (BBA)—Molecular Cell Research* 1803, 333-341, (2010); Randow, F. & Seed, B. Endoplasmic reticulum chaperone gp96 is required for innate immunity but not cell viability. *Nat Cell Biol* 3, 891-896, (2001); Saitoh, T. et al. Down-Regulation of Cell Surface Insulin Receptor and Insulin Receptor Substrate-1 Phosphorylation by Inhibitor of 90-kDa Heat-Shock Protein Family: Endoplasmic Reticulum Retention of Monomeric Insulin Receptor Precursor with Calnexin in Adrenal Chromaffin Cells. *Molecular Pharmacology* 62, 847-855, (2002); Yang, Y. et al. Heat shock protein gp96 is a master chaperone for toll-like receptors and is important in the innate function of macrophages. *Immunity* 26, 215-226, (2007)).

Since these clients play key roles in cell-to-cell communication and adhesion, Grp94-selective inhibitors may disrupt malignant progression by preventing metastasis, migration, immunoevasion and/or cell adhesion. (Ostrovsky, O., Eletto, D., Makarewich, C., Barton, E. R. & Argon, Y. Glucose regulated protein 94 is required for muscle differentiation through its control of the autocrine production of insulin-like growth factors. *Biochimica et Biophysica Acta (BBA)—Molecular Cell Research* 1803, 333-341, (2010); Randow, F. & Seed, B. Endoplasmic reticulum chaperone gp96 is required for innate immunity but not cell viability. *Nat Cell Biol* 3, 891-896, (2001); Saitoh, T. et al. Down-Regulation of Cell Surface Insulin Receptor and Insulin Receptor Substrate-1 Phosphorylation by Inhibitor of 90-kDa Heat-Shock Protein Family: Endoplasmic Reticulum Retention of Monomeric Insulin Receptor Precursor with Calnexin in Adrenal Chromaffin Cells. *Molecular Pharmacology* 62, 847-855, (2002); Yang, Y. et al. Heat shock protein gp96 is a master chaperone for toll-like receptors and is important in the innate function of macrophages. *Immunity* 26, 215-226, (2007); Belfiore, A., Pandini, G., Vella, V., Squatrito, S. & Vigneri, R. Insulin/IGF-I hybrid receptors play a major role in IGF-I signaling in thyroid cancer. *Biochimie* 81, 403-407, (1999); Chavany, C. et al. p185 Binds to GRP94 in Vivo. *Journal of Biological Chemistry* 271, 4974-4977, (1996); Moorehead, R. A., Sanchez, O. H., Baldwin, R. M. & Khokha, R. Transgenic overexpression of IGF-II induces spontaneous lung tumors: a model for human lung adenocarcinoma. *Oncogene* 22, 853-857, (2003); Supino-Rosin, L., Yoshimura, A., Yarden, Y., Elazar, Z. & Neumann, D. Intracellular Retention and Degradation of the Epidermal Growth Factor Receptor, Two Distinct Processes Mediated by Benzoquinone Ansamycins. *Journal of Biological Chemistry* 275, 21850-21855, (2000)). Interestingly, many of these Grp94-dependent clients have also been identified as key contributors to inflammatory disorders such as rheumatoid arthritis, diabetes and asthma. (MvLaughlin, M., Alloza, I. & Vandenbroeck, K. Different chaperone usage by IL-12 and IL-23 during their assembly reveals novel targets for intervention with cytokine secretion in neuroinflammation. *Neuroimmunol.* 203, 268, (2008); Zuany-Amorim, C., Hastewell, J. & Walker, C. Toll-like receptors as potential therapeutic targets for multiple diseases. *Nat Rev Drug Discov* 1, 797-807, (2002); McLaughlin, M. & Vandenbroeck, K. The endoplasmic reticulum protein folding factory and its chaperones: new targets for drug discovery? *British Journal of Pharmacology* 162, 328-345, (2011); Randow, F. & Seed, B. Endoplasmic reticulum chaperone gp96 is required for innate immunity but not cell viability. *Nat Cell Biol* 3, 891-896, (2001)). Therefore, the ability to develop a Grp94-selective inhibitor may not only provide a new paradigm for Hsp90 inhibition, but may also provide new opportunities for the treatment of diseases other than cancer.

The biological roles manifested by Grp94 have been primarily elucidated through the use of RNAi induced Grp94 knockdown, immunoprecipitation experiments, or through pan-inhibition of all four Hsp90 isoforms. A selective small molecule inhibitor of Grp94 would provide an alternative and powerful method for further elucidation of the roles manifested by Grp94, as well as the identity of other Grp94-dependent processes/substrates. Recently, the co-crystal structures of the chimeric inhibitor, radamide (RDA), bound to the N-terminal domain of both the yeast ortholog of cytosolic Hsp90 (yHsp82N, PDB: 2FXS) and the canine ortholog of Grp94 (cGrp94NΔ41, PDB: 2GFD) were described. (Immormino, R. M. et al. Different Poses for Ligand and Chaperone in Inhibitor-Bound Hsp90 and GRP94: Implications for Paralog-Specific Drug Design. *J. Mol. Biol.* 388, 1033-1042, (2009)). Utilizing a structure-based approach that relied upon these co-crystal structures, a new class of inhibitors that target Grp94 has been developed.

Example 1

Design and Synthesis of Grp94 Isoform Selective Inhibitors

Co-crystal structures of the natural products, geldanamycin (GDA) and radicicol (RDC), bound to the highly conserved N-terminal region have been solved. (Dollins, D. E., Immormino, R. M. & Gewirth, D. T. Structure of unliganded GRP94, the ER Hsp90: Basis for nucleotide-induced conformational change. *J. Biol. Chem.* 280, 30438-30447, (2005); Dollins, D. E., Warren, J. J., Immormino, R. M. & Gewirth, D. T. Structures of GRP94-nucleotide complexes reveal mechanistic differences between the hsp90 chaperones. *Mol. Cell* 28, 41-56, (2007); Immormino, R. M. et al. Ligand-induced conformational shift in the N-terminal domain of GRP94, an Hsp90 chaperone. *J. Biol. Chem.* 279, 46162-46171, (2004); Immormino, R. M. et al. Different Poses for Ligand and Chaperone in Inhibitor-Bound Hsp90 and GRP94: Implications for Paralog-Specific Drug Design. *J. Mol. Biol.* 388, 1033-1042, (2009); Soldano, K. L., Jivan, A., Nicchitta, C. V. & Gewirth, D. T. Structure of the N-terminal domain of GRP94. Basis for ligand specificity and regulation. *J. Biol. Chem.* 278, 48330-48338, (2003)).

Figure 2:
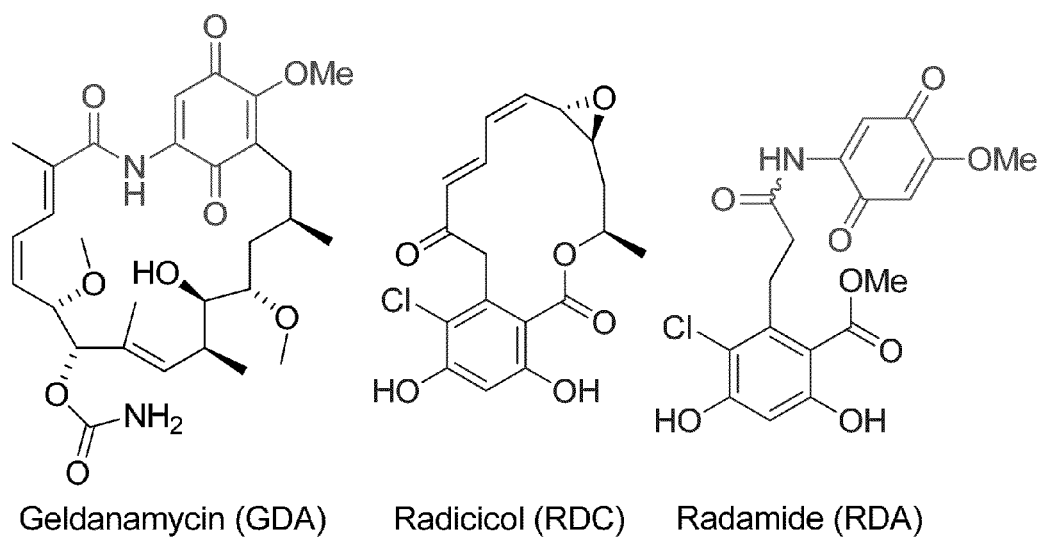
FIG. 2 is a series of images depicting the chimeric approach to Hsp90 inhibition.

Subsequent studies showed that chimeric inhibitors containing the quinone moiety of GDA and the resorcinol of RDC (FIG. 2) also target this domain. (Clevenger, R. C. & Blagg, B. S. J. Design, Synthesis, and Evaluation of a Radicicol and Geldanamycin Chimera, Radamide. *Org. Lett.* 6, 4459-4462, (2004); Hadden, M. K. & Blagg, B. S. J. Synthesis and Evaluation of Radamide Analogues, A Chimera of Radicicol and Geldanamycin. *J. Org. Chem.* 74, 4697-4704, (2009); Shen, G., Wang, M., Welch, T. R. & Blagg, B. S. J. Design, Synthesis, and Structure Activity Relationships for Chimeric Inhibitors of Hsp90. *J. Org. Chem.* 71, 7618-7631, (2006); Shen, G. & Blagg, B. S. J. Radester, a Novel Inhibitor of the Hsp90 Protein Folding Machinery. *Org. Lett.* 7, 2157-2160, (2005)).

Three chimeric scaffolds were identified as Hsp90 inhibitors that manifested anti-proliferative activity against various cancer cell lines. Radamide (RDA) was the first chimera produced, and the first co-crystallized with cytosolic Hsp90 from yeast (yHsp82) and Grp94 from canine (cGrp94NΔ41) by the Gewirth laboratory. (Immormino, R. M. et al. Different Poses for Ligand and Chaperone in Inhibitor-Bound Hsp90 and GRP94: Implications for Paralog-Specific Drug Design. *J. Mol. Biol.* 388, 1033-1042, (2009); Clevenger, R. C. & Blagg, B. S. J. Design, Synthesis, and Evaluation of a Radicicol and Geldanamycin Chimera, Radamide. *Org. Lett.* 6, 4459-4462, (2004); Hadden, M. K. & Blagg, B. S. J. Synthesis and Evaluation of Radamide Analogues, A Chimera of Radicicol and Geldanamycin. *J. Org. Chem.* 74, 4697-4704, (2009)).

Analyses of the two co-crystal structures (FIG. 3A-C) revealed the resorcinol ring to bind similarly in both isoforms, making a direct hydrogen bond with the conserved aspartic acid residue (Asp79 in yHsp82 and Asp149 in cGrp94NΔ41) involved in ATP binding. However, the quinone moiety was found to bind yHsp82N in a linear, trans-amide conformation, which was distinct from one conformation observed in the cGrp94NΔ41 co-crystal structure. Upon binding cGrp94NΔ41, two opposing conformations of RDA were observed (50% occupancy each): One conformation exhibited a cis-amide orientation and projected the quinone moiety into a hydrophobic pocket that exists solely in Grp94 due to a five amino acid insertion into the primary sequence. The second conformation of RDA observed in the RDA.cGrp94NΔ41 co-crystal structure presented the amide in a trans-configuration and projected the quinone toward the outside of the binding pocket, similar to that observed for RDA in the yHsp82N co-crystal structure. (Immormino, R. M. et al. Different Poses for Ligand and Chaperone in Inhibitor-Bound Hsp90 and GRP94: Implications for Paralog-Specific Drug Design. *J. Mol. Biol.* 388, 1033-1042, (2009)). Interestingly, RDA was found to exhibit an approximately 2-fold higher binding affinity for full-length Grp94 than yHsp82.

Figure 3:
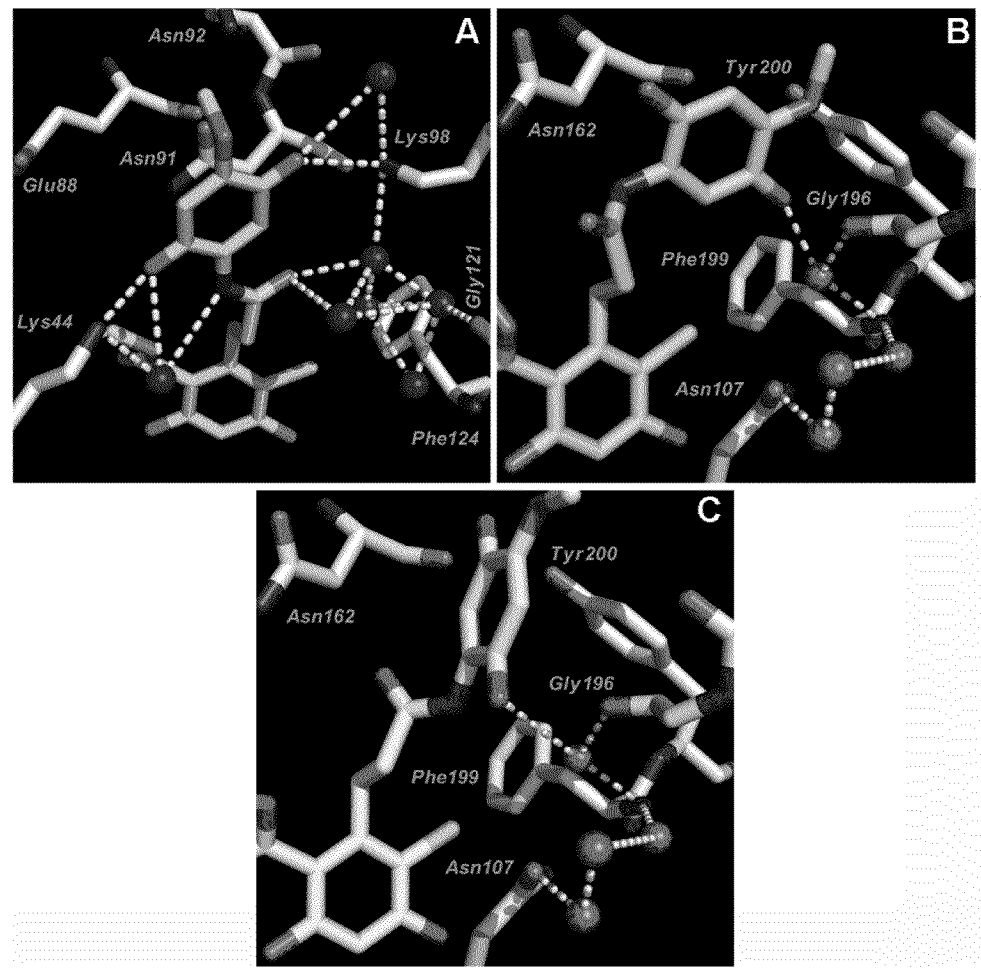
FIGS. 3A-C are a series of images depicting RDA quinone hydrogen-bonding network comparison between yHsp82N (A) and cGrp94NΔ41 with RDA cis-amide (B) and RDA trans-amide (C). Spheres represent water molecules, while hashed lines represent a hydrogen-bonding interaction.

Further analyses of the RDA.yHsp82N co-crystal structure revealed the quinone to mediate an intricate hydrogen-bonding network, whereas its interaction with cGrp94NΔ41 was limited (FIG. 3). For example, in the RDA.yHsp82N structure, direct hydrogen bonds between the RDA quinone and Lys98 and Lys44 were observed. In contrast, no direct hydrogen bonds were observed between cGrp94NΔ41 and the cis-amide quinone (FIG. 3B), suggesting that functionalities on the quinone ring may be dispensable for Grp94 binding, but obligatory for cytosolic Hsp90 binding. In addition, this Grp94 hydrophobic pocket contains aromatic amino acids (Phe199, Tyr200 and Trp223) that are likely to facilitate π-stacking interactions, and could be utilized for the design of inhibitors that exhibit increased selectivity and affinity for Grp94 over cytosolic Hsp90. Although the primary sequences and ATP-binding pockets are highly homologous (>70% similar, 55% identical), this minor disparity was exploited for the rational design of Grp94 inhibitors. (Sreedhar, A. S., Kalmar, E. & Csermely, P. Hsp90 isoforms: functions, expression and clinical importance. *FEBS Lett.* 562, 11-15, (2004)).

The design elements were focused on the conformation of RDA when bound to cGrp94NΔ41 versus yHsp82N, the dispensability of the quinone moiety, and the hydrophobicity of the Grp94 π-rich pocket. Based on these observations, the inventors hypothesized that inhibitors containing a more hydrophobic surrogate of the quinone linked to the resorcinol through a cis-amide bioisostere would provide compounds that inhibit Grp94 selectively.

Multiple bioisosteres exist for the cis-amide functionality, however in this instance, those exhibiting a conformational bias rather than a specific physical property were considered. Observation that the cis-amide conformation of RDA bound to cGrp94NΔ41 projects the quinone moiety into the Grp94 hydrophobic pocket suggested that cis-olefins, carbocycles or heterocycles may represent appropriate surrogates. In the end, imidazole was chosen based on the inclusion of a hydrogen bond acceptor in the same location as the amide carbonyl, which could provide complementary interactions with Asn162 (FIG. 3).

Since no direct hydrogen-bonding interactions exist between the quinone and cGrp94NΔ41, and several π-rich amino acids (Phe199, Tyr200, and Trp223) reside in this secondary pocket, the utilization of an aromatic ring in lieu of the quinone was pursued. A phenyl ring was envisioned to provide the desired π-interactions with Phe199, Tyr200, and Trp223 while providing a rational starting point for the development of Grp94 selective inhibitors. The imidazole linker was expected to project the phenyl ring similar to that observed for the RDA quinone, and therefore the tether between the imidazole and phenyl moiety was analyzed by computational examination. Compounds 1-5 were designed as hypothetical Grp94 inhibitors that contained the three aspects envisioned to be important for inhibition: 1) A resorcinol ring to ensure N-terminal inhibition and correct orientation within in the ATP-binding pocket, 2) a predisposed cis-amide conformation that projected the phenyl appendage toward the unique Grp94 binding pocket, and 3) a hydrophobic, π-rich surrogate for the quinone. The latter of which would be incapable of providing the requisite hydrogen-bonding interactions with cytosolic Hsp90, and should therefore facilitate binding to the π-rich region of Grp94.

Utilizing Surflex molecular docking software, analogs 1-5 were docked to the RDA.cGrp94NΔ41 complex (PDB: 2GFD). As shown in Scheme 1, the Surflex binding scores for Compounds 1 and 2 were 1-2 units higher than that of RDA, suggesting binding affinities of 10-100-fold higher for cGrp94NΔ41, respectively. Furthermore, 1-5 failed to dock to the RDA.yHsp82N complex (PDB: 2FXS), supporting the hypothesis that these phenyl imidazole analogs may exhibit selective inhibition. Although 1 and 2 were the only compounds predicted to bind cGrp94NΔ41, prior studies demonstrated the Grp94 lid region to undergo significant variations that are capable of accommodating various ligand sizes and chemotypes. Unfortunately, available modeling programs could not account for this phenomenon and therefore, all five analogs were constructed. Aldehyde 6 (Scheme 1), which was utilized during the synthesis of RDA, was readily available and allowed for the rapid preparation of analogs. (Clevenger, R. C. & Blagg, B. S. J. Design, Synthesis, and Evaluation of a Radicicol and Geldanamycin Chimera, Radamide. *Org. Lett.* 6, 4459-4462, (2004); Hadden, M. K. & Blagg, B. S. J. Synthesis and Evaluation of Radamide Analogues, A Chimera of Radicicol and Geldanamycin. *J. Org. Chem.* 74, 4697-4704, (2009)).

As shown in Scheme 1, a Radziszewski-like condensation of aldehyde 6 with the requisite aniline/primary amine in the presence of glyoxal and ammonium bicarbonate provided the desired compounds as protected silyl ethers. (Baldwin, J. J. et al. β-Adrenergic blocking agents with acute antihypertensive activity. *J. Med. Chem.* 22, 687-694, (1979); Radziszewski, B. Glyoxaline and its homologues. *Ber.* 15, 2706-2708, (1882)). Addition of tetrabutylammonium fluoride to the reaction mixture yielded the desilylated compounds 1-5 in moderate yields.

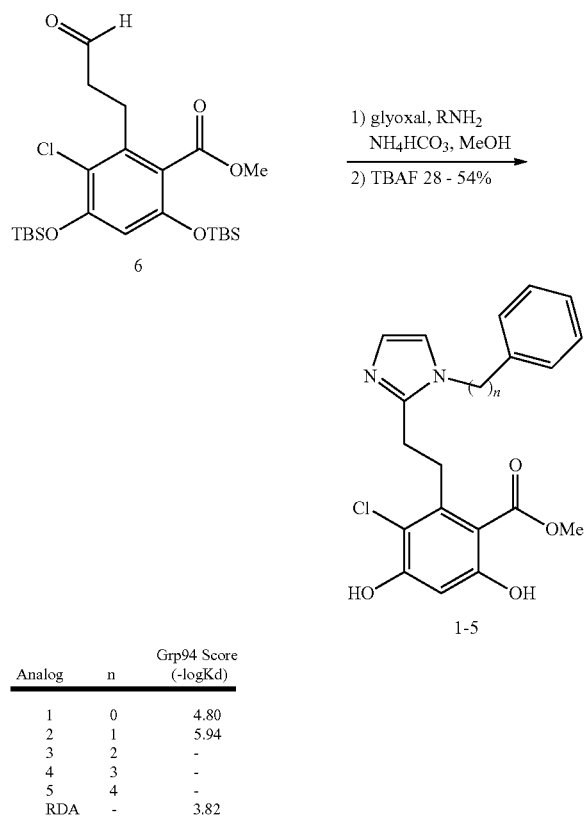

| Analog | n | Grp94 Score (-logKd) |
|---|---|---|
| 1 | 0 | 4.80 |
| 2 | 1 | 5.94 |
| 3 | 2 | - |
| 4 | 3 | - |
| 5 | 4 | - |
| RDA | - | 3.82 |

Effect on Trafficking of a Toll-Like Receptor

Upon preparation of 1-5, biological studies commenced to validate the hypothesis that imidazoles containing a phenyl moiety provide Grp94 inhibition. Unlike cytosolic Hsp90 inhibitors that exhibit anti-proliferative effects, RNAi experiments have shown that in culture, cell viability is unhampered by knockdown of Grp94. (Randow, F. & Seed, B. Endoplasmic reticulum chaperone gp96 is required for innate immunity but not cell viability. *Nat. Cell Biol.* 3, 891-896, (2001)). Thus, a functional assay was necessary to determine Grp94 inhibition.

Grp94 is required for the functional maturation and trafficking of select TLRs. (Yang, Y. et al. Heat shock protein gp96 is a master chaperone for toll-like receptors and is important in the innate function of macrophages. *Immunity* 26, 215-226, (2007); Randow, F. & Seed, B. Endoplasmic reticulum chaperone gp96 is required for innate immunity but not cell viability. *Nat. Cell Biol.* 3, 891-896, (2001)). Therefore, TLR dependence upon Grp94 was utilized to develop an assay to quantify Grp94 inhibition. As proof of concept, HEK293 cells were stably transfected to express Grp94 directed or scrambled shRNA. Both cell lines were then transfected with a plasmid encoding expression of the Toll protein, the *drosophila* homologue of the interleukin 1 receptor and the founding member of the TLR family. Grp94 knockdown prevented presentation of the Toll receptor at the cell surface (FIG. 4A) as indicated by immunostaining and fluorescence microscopy. In order to investigate this inhibition of trafficking, cells were permeabilized with Triton X to effect intracellular staining for Toll. Results clearly indicated that the Toll receptor was expressed in the absence of Grp94, but unable to be trafficked to the cell membrane. Western blot analyses of lysates from Grp94 knockdown cells indicated a difference in the glycosylation pattern of the Toll protein, providing evidence for impaired trafficking to the cell membrane (FIG. 4B). (Istomin, A. & Godzik, A. Understanding diversity of human innate immunity receptors: analysis of surface features of leucine-rich repeat domains in NLRs and TLRs. *BMC Immunology* 10, 48, (2009); Qiu, L., Song, L., Xu, W., Ni, D. & Yu, Y. Molecular cloning and expression of a Toll receptor gene homologue from Zhikong Scallop, Chlamys farreri. *Fish Shellfish Immun.* 22, 451-466, (2007); Sun, J. et al. Structural and Functional Analyses of the Human Toll-like Receptor 3. *J. Biol. Chem.* 281, 11144-11151, (2006); Weber, A. N. R., Morse, M. A. & Gay, N. J. Four N-linked Glycosylation Sites in Human Toll-like Receptor 2 Cooperate to Direct Efficient Biosynthesis and Secretion. *J. Biol. Chem.* 279, 34589-34594, (2004)). This may indicate that Grp94 interacts with a chaperone or partner protein that is involved in the glycosylation of its clients.

Figure 4:
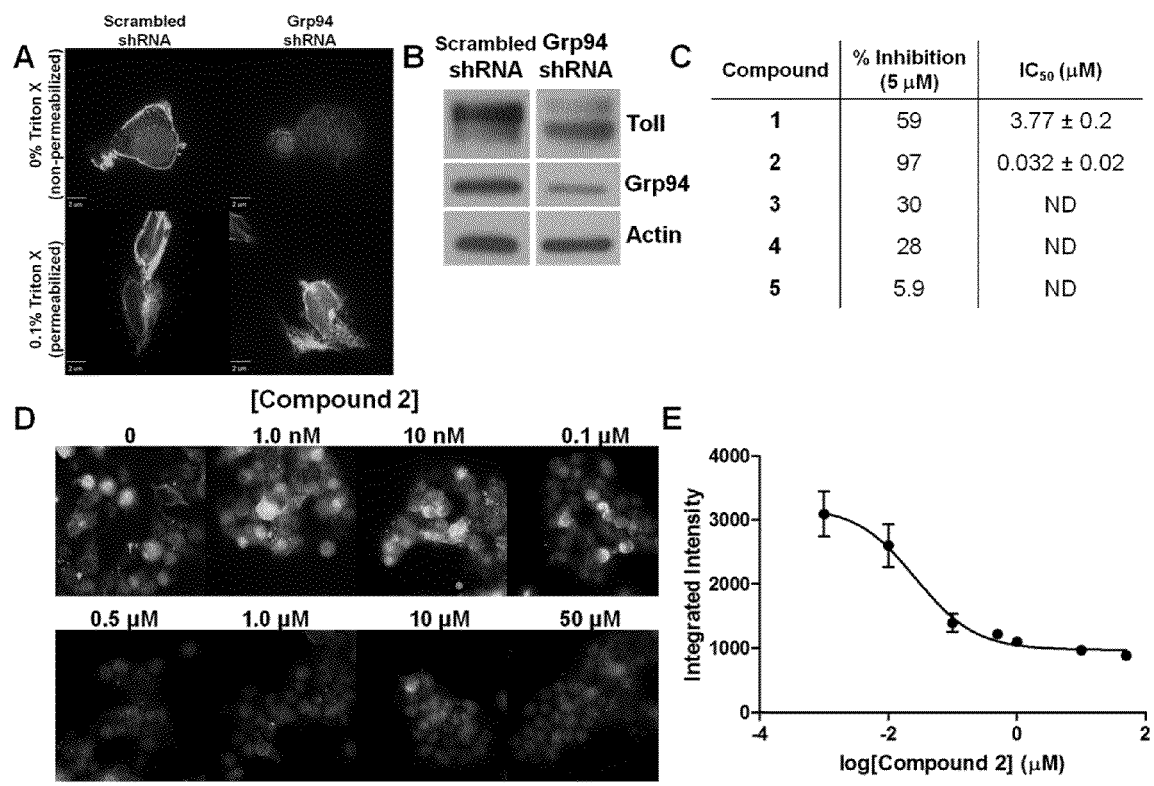
FIGS. 4A-E are a series of images depicting representative fluorescence confocal microscopy images of HEK293 cells stably transfected to produce either scrambled shRNA or Grp94-targeted shRNA and transfected to express the Toll receptor (DAPI, 100×TIRF oil immersion (A); Western blot analysis of cells treated as in A (B); Table of activities for compounds 1-5 to inhibit the trafficking of toll (error bars=+/−SEM for at least 100 different cell populations (C); Representative epifluorescence microscopy images of HEK293 cells transfected to express the Toll receptor (green)

Once functional knockdown of Grp94 was established, and a reduced cell surface expression of Toll observed, this assay served as readout for Grp94 inhibition. HEK293 cells were transfected with the same Toll-expressing plasmid, and subsequently exposed to compounds 1-5 for 24 h prior to surface staining. The extent of surface expression was then quantified by measuring fluorescence intensity at the cell surface with Cell Profiler. (Carpenter, A. et al. CellProfiler: image analysis software for identifying and quantifying cell phenotypes. *Genome Biol.* 7, R100, (2006)). A dose-response curve for each of the compounds that inhibited at least 50% of Toll trafficking at 5 μM was generated to obtain $IC_{50}$ values (FIG. 4C). Representative fluorescent microscopic images and a dose-response curve are shown for compound 2 in FIG. 4. Interestingly, the observed $IC_{50}$ values for this series of compounds correlated well with the increased binding affinities predicted by Surflex docking scores, supporting the proposed mode of binding. To ensure that compound 2 demonstrates selectivity for Grp94 versus cytosolic Hsp90 (Hsp90α and Hsp90β), the inventors investigated the effect of compound 2 on both cell proliferation and the stability of Hsp90-obligate clients, two well-established methods for the evaluation of Hsp90α/β inhibitors.

Inhibition of IGF-II Secretion by Compound 2

IGF-II is a second well-defined Grp94-dependent client protein and active Grp94 is required for the secretion of IGF-II (Ostrovsky et al., 2009). It has been previously demonstrated that pan-Hsp90 inhibitors, such as 17-AAG, prevent the secretion of IGF-II in serum-starved C2C12 myoblast cells. (Wanderling, S. et al. GRP94 Is Essential for Mesoderm Induction and Muscle Development Because It Regulates Insulin-like Growth Factor Secretion. *Mol. Biol. Cell* 18, 3764-3775, (2007); Ostrovsky, O., Eletto, D., Makarewich, C., Barton, E. R. & Argon, Y. Glucose regulated protein 94 is required for muscle differentiation through its control of the autocrine production of insulin-like growth factors. *BBA—Mol. Cell Res.* 1803, 333-341, (2010); Ostrovsky, O., Ahmed, N. T. & Argon, Y. The Chaperone Activity of GRP94 Toward Insulin-like Growth Factor II Is Necessary for the Stress Response to Serum Deprivation. *Mol. Biol. Cell* 20, 1855-1864, (2009)). Accordingly, serum-starved C2C12 cells were treated with increasing concentrations of compound 2 and the secretion of IGF-II was measured by ELISA (FIG. 5A). Approximately 60% reduction of IGF-II was observed already at 10 µM of 2, while little effect on cell viability was observed (FIG. 5B). The effect on IGF-II secretion is consistent with previous observations using pan-Hsp90 inhibitors, while the lack of effect on cell viability by Compound 2 indicates that this compound is working through a Grp94-dependent mechanism and does not exhibit pan-inhibition.

Effect on Grp94 Conformation

Prior studies have shown that occupation of the Grp94 N-terminal ATP binding pocket by inhibitors results in an altered conformation of this domain (ref). Anti-Grp94 (9G10) is an antibody that recognizes the acidic region (residues 290-350) in the second domain of Grp94. Occupation of the ATP binding site causes a conformational switch in this region and prevents the 9G10 antibody from recognizing Grp94. (Vogen, S. et al. Radicicol-sensitive Peptide Binding to the N-terminal Portion of GRP94. *J. Biol. Chem.* 277, 40742-40750, (2002)). Therefore, lysates of C2C12 cells treated with increasing concentrations of compound 2 were immunoprecipitated to assess whether it induces a conformational switch in Grp94. As observed in FIG. 6, compound 2 induces a conformational switch in Grp94, as the 9G10 antibody is unable to recognize and immunoprecipitate the Grp94 in cells treated with 2. This result parallels the IGF-II secretion data shown in FIG. 5, suggesting that an alteration in Grp94 conformation is incompatible with IGF-II secretion. Interestingly, this activity of Grp94 inhibitors appears to be cell-specific, as analogous experiments performed in CHO cells failed to show an effect on the conformation of Grp94 (data not shown).

Hsp90α/β Inhibitory Activity of Compound 2

As previously mentioned, it has been shown that Grp94 is not essential for tissue culture cell viability (Wanderling et al., 2006). In contrast, loss of functional Hsp90α or Hsp90β results in cell death. Therefore, the inventors investigated the anti-proliferative effects of compounds 1-5 against two breast cancer cells, MCF7 (ER+) and SKBR3 (Her2 overexpressing, ER−), and against the non-transformed HEK293 cells. None of the compounds evaluated manifested anti-proliferative activity at 100 µM, indicating these compounds do not target Hsp90α or Hsp90β. To support these findings, western blot analyses of Hsp90α/β client proteins were performed from HEK293 cell lysates. Prototypical pan-Hsp90 inhibitors induce proteasome-mediated degradation of Hsp90α/β client substrates. (Blagg, B. S. J. & Kerr, T. D. Hsp90 inhibitors: small molecules that transform the Hsp90 protein folding machinery into a catalyst for protein degradation. *Med. Res. Rev.* 26, 310-338, (2006)).

Figure 7:
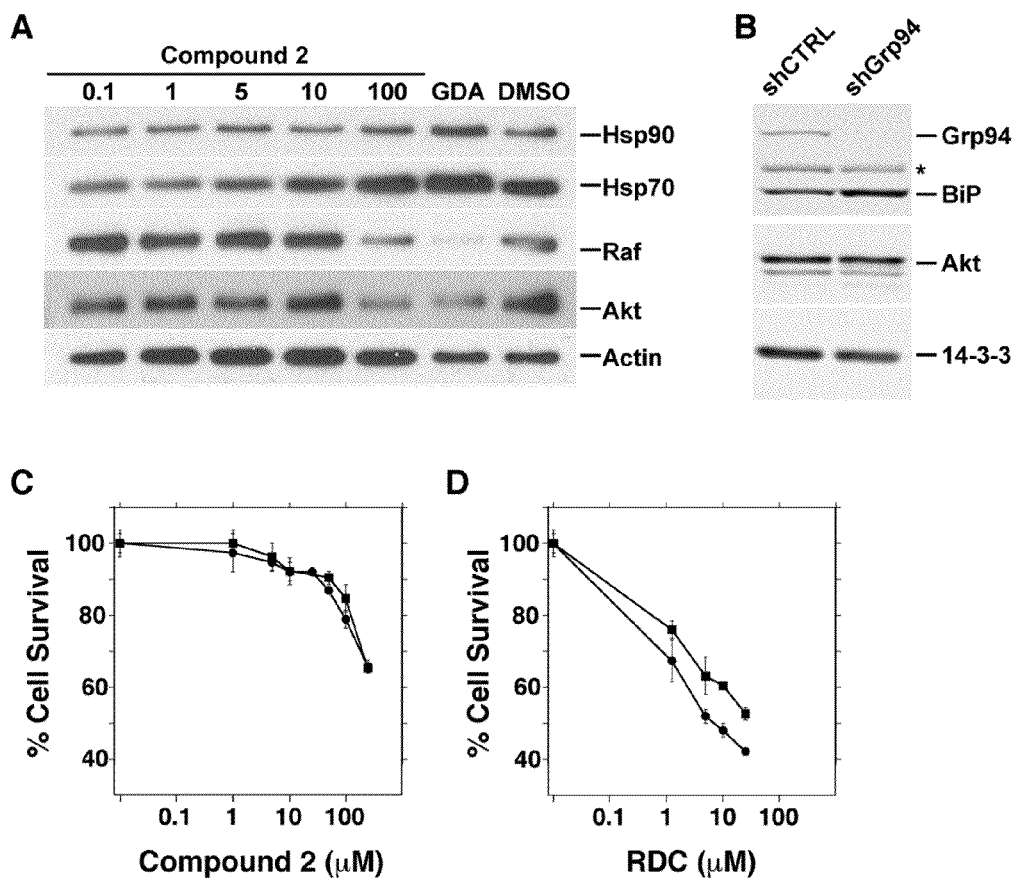

As shown in FIG. 7, Compound 2 does not induce the degradation of Raf or Akt, two well-documented Hsp90α/β-dependent client proteins until 100 µM concentration (see also FIG. 8). (Basso, A. D. et al. Akt Forms an Intracellular Complex with Heat Shock Protein 90 (Hsp90) and Cdc37 and Is Destabilized by Inhibitors of Hsp90 Function. *J. Biol. Chem.* 277, 39858-39866, (2002); Grbovic, O. M. et al. V600E B-Raf requires the Hsp90 chaperone for stability and is degraded in response to Hsp90 inhibitors. *P. Natl. Acad. Sci.* 103, 57-62, (2006); da Rocha Dias, S. et al. Activated B-RAF Is an Hsp90 Client Protein That Is Targeted by the Anticancer Drug 17-Allylamino-17-Demethoxygeldanamycin. *Cancer Res.* 65, 10686-10691, (2005)). At this concentration, induction of HSP70, similar to the one induced by GDA, is presumably mediated by targeting of cytosolic Hsp90. As shown in FIG. 7B, the effect on Akt cannot be attributed to ablation of GRP94.

The inventors also tested the cytotoxicity of compound 2 in cells that are either GRP94-sufficient or -deficient and compared it to the cytotoxicity of RDC. As shown in FIG. 7C-D, compound 2 is much less toxic: the IC50 for HeLa cell viability is >250 µM, while RDC already reaches this level at 8 µM. In either case, the cytotoxicity is not attributable to inhibition of GRP94, because cells responded equally regardless of the presence of GRP94 (FIG. 7C-D). Similar results were obtained with other cell lines (e.g. C2C12 in FIG. 6).

At the lower concentration range Compound 2 inhibits the presentation of the Grp94-dependent Toll receptor at approximately 30 nM and does not affect cytoplasmic proteins until 100 µM in HEK293 cells, providing evidence for Grp94 selective inhibition. To further understand the implications of Grp94-selective inhibition, compound 2 was analyzed in other Grp94-dependent processes.

Induction of BiP Expression

Inhibition of Hsp90 is also known to induce expression of Hsp70 and this response is useful as a diagnostic tool (ref and FIG. 7). A parallel response exists when Grp94 expression is ablated by RNAi, or when its activity is inhibited by RDC or 17-AAG: a transcriptional response is initiated that leads to upregulation of expression of BiP, the ER member of the Hsp70 family (Eletto et al., submitted). The inventors therefore assessed the ability of 2 to cause BiP up-regulation, in comparison to pan-Hsp90 inhibitors. As shown in FIG. 8, treatment of C2C12 cells with 0-75 µM of compound 2 did not lead to up-regulation of BiP, while treatments with 10 µM Rad (or 25 µM of 17-AAG, data not shown) did cause BiP up-regulation. Only at concentrations above 200 µM did compound 2 resemble RDC and induce BiP expression. However, at these concentrations, the compound also destabilized Akt, a hallmark of inhibition of cytosolic Hsp90 (FIG. 8). The inability of 2 to upregulate BiP at the 0-75 µM concentration range was surprising, because this transcriptional response was shown to be a property of Grp94 ablation and not Hsp90 (Eletto et al., submitted).

Effect on *Drosophila* Development

Previous studies have demonstrated that Gp93, the *Drosophila* ortholog of Grp94 is an essential gene. (Maynard, J. C. et al. Gp93, the *Drosophila* GRP94 ortholog, is required for gut epithelial homeostasis and nutrient assimilation-coupled growth control. *Dev. Biol.* 339, 295-306, (2010)). In the *Drosophila* model, maternal Gp93 is sufficient to support embryogenesis in Gp93 homozygous null embryos. In the absence of zygotic expression of Gp93, however, larvae display a pronounced growth defect, commensurate with disrupted gut epithelial morphology, decreased gut nutrient uptake, and marked aberrations in copper cell structure and function. As a consequence, loss of Gp93 expression is larval lethal in *Drosophila*.

Figure 9:
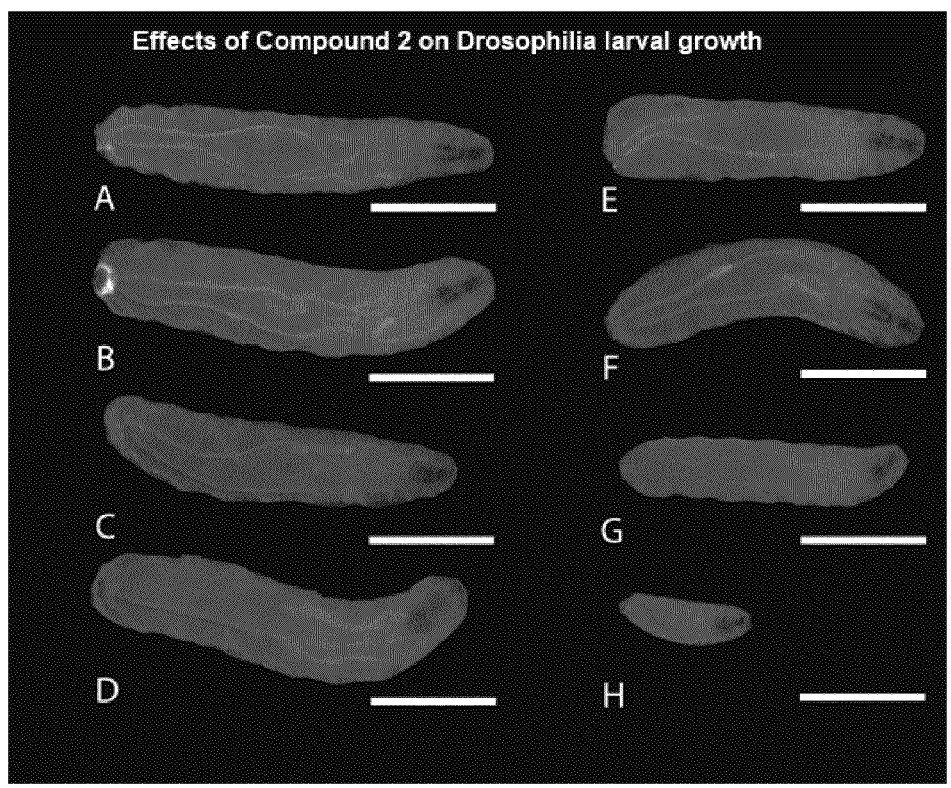

To determine the effects of compound 2 on *Drosophila* larval growth, first instar wild type (w1118) larvae were placed onto fly food supplemented with either no supplement (A), 0.1% (B), 0.3% (C), or 0.5% (D) DMSO (vehicle controls) or fly food supplemented with 250 µg/ml (E), 500 µg/ml (F), 750 µg/ml (G) or 1 mg/ml (H) compound 2. As is evident from the micrographs of representative larvae, dietary uptake of 2 was associated with a dramatic growth phenotype (FIG. 9). In parallel experiments, larval gut tissue was obtained from each of the feeding conditions and gut epithelial morphology evaluated by fluorescence microscopy. No grossly discernible effects on copper cell structure were observed, however, indicating that under these feeding conditions, the inhibition of Gp93 function was incomplete (data not shown). Pharmacokinetic studies of compound absorption and metabolism may provide addition insights into this partial phenotypic behavior.

Hsp90 inhibitors have been the subject of intense pharmaceutical research, not only for cancer, but also neurodegeneration. (Workman, P., Burrows, F., Neckers, L. & Rosen, N. Drugging the cancer chaperone Hsp90: Combinatorial therapeutic exploitation of oncogene addiction and tumor stress. *Ann. NY Acad. Sci.* 1113, 202-216, (2007); Banerji, U. Heat shock protein 90 as a drug target: some like it hot. *Clin. Cancer Res.* 15, 9-14, (2009); Benson, J. D. et al. Validating cancer drug targets. *Nature* 441, 451-456, (2006); Isaacs, J. S., Xu, W. S. & Neckers, L. Heat shock protein as a molecular target for cancer therapeutics. *Cancer Cell* 3, 213-217, (2003); Li, Y., Schwartz, S. J. & Sun, D. New developments in Hsp90 inhibitors as anti-cancer therapeutics: mechanisms, clinical perspective and more potential. *Drug Resist. Update* 12, 17-27, (2009); Neckers, L. Hsp90 inhibitors as novel cancer chemotherapeutic agents. *Trends Mol. Med.* 8, S55-S61, (2002); Workman, P. & Billy, E. d. Putting the heat on cancer. *Nat. Med.* 13, 1415-1417, (2007); Peterson, L. B. & Blagg, B. S. J. To fold or not to fold: modulation and consequences of Hsp90 inhibition. *Future Med. Chem.* 1, (2009)). All Hsp90 inhibitors that have reached clinical trials bind to the Hsp90 N-terminal ATP-binding pocket and demonstrate pan-Hsp90 inhibition, i.e. they inhibit all human Hsp90 isoforms simultaneously. (Biamonte, M. A. et al. Heat shock protein 90: inhibitors in clinical trials. *J. Med. Chem.* 53, 3-17, (2010); Kim, Y. S. et al. Update on Hsp90 inhibitors in clinical trial. *Curr. Top. Med. Chem.* 9, 1479-1492, (2009); Taldone, T., Gozman, A., Maharaj, R. & Chiosis, G. Targeting Hsp90: small-molecule inhibitors and their clinical development. *Curr. Opin. Pharmacol.* 8, 370-374, (2008)). Toxicities and off-target effects resulting from Hsp90 inhibition may therefore result from pan-inhibition. The design of Hsp90 isoform-selective inhibitors provides valuable pharmacological tools to dissect the roles of each isoform and may lead to more clinically useful inhibitors.

Comparing the crystal structures of several known Hsp90 inhibitors bound to either cytosolic Hsp90 or to the ER-resident Grp94 provided a rationale design for selective Grp94 inhibitors. Using structure-based drug design, five compounds were identified as potential leads that contain a phenyl ring appended to an imidazole ring, which serves as a cis-amide bioisostere. The predisposed orientation of the phenyl ring was postulated to allow interactions with the unique Grp94 π-rich pocket. Since Grp94 has previously been shown to be responsible for the trafficking of TLRs to the cell membrane, this activity was used as a functional assay for Grp94 inhibition. Of the five compounds evaluated, compound 2 manifested the best activity in this assay (35 nM). In subsequent, direct readout assays, including an in-cell conformational assay, compound 2 affected Grp94 itself at the same concentration as that needed to inhibit chaperone activity. (Yang, Y. et al. Heat shock protein gp96 is a master chaperone for toll-like receptors and is important in the innate function of macrophages. *Immunity* 26, 215-226, (2007)).

Once the Grp94 inhibitory activity of compound 2 was established by these parameters, the inventors evaluated the isoform selectivity of the compound. Inhibitors of cytosolic Hsp90 (Hsp90α/β) manifest antiproliferative activity in cell culture. At the concentrations where the previous assays showed activity of compound 2, there were no cytotoxic effects on any of the cell lines tested. In addition, compound 2 had no effect on the prototypical Hsp90α/β client kinases Akt or Raf until concentrations 100× of $IC_{50}$ of the chaperone activity. Therefore, compound 2 has considerable selectivity for GRP94 over Hsp90α/β, perhaps explaining its low toxicity. Lastly, compound 2 clearly stunted the growth of *drosophila* larvae in a dose-dependent manner, suggesting that it may be a useful GRP94 inhibitor in vivo.

Materials and Methods

General Method for the Synthesis of Compounds 1-5

Aldehyde 6 (1 equiv.) was dissolved in wet MeOH at 25° C. The required aniline/amine (1 equiv.) was added dropwise via a syringe to the reaction flask followed by addition of ammounim bicarbonate (1 equiv.). Glyoxal (1 equiv.) was then added dropwise via a syringe and the reaction was allowed to stir at 25° C. for 8 h. Upon complete conversion of the aldehyde, as observed by thin-layer chromatography, tetrabutylammonium fluoride was added dropwise via syringe and the reaction was allowed to stir at 25° C. for 30 min, at which time, the reaction was quenched with sat. aq. $NH_4Cl$ and extracted with EtOAc. The organic layers were combined, dried over $Na_2SO_4$, and concentrated in vacuo. All compounds were purified via flash chromatography utilizing 95:5 (DCM:MeOH) as the eluent. Yields and characterization for all compounds are provided in the supplementary information.

Cell Culture

HEK293 and C2C12 cells were maintained in DMEM supplemented with non-essential amino acids, L-glutamine (2 mM), streptomycin (500 µg/mL), penicillin (100 units/mL), and 10% FBS. Cells were grown to confluence in a humidified atmosphere (37° C., 5% CO2). Preparation of Grp94 or scrambled shRNA stable transfectants (Nicchitta). C2C12 Cells were induced to differentiate into myoblasts as described in Argon.

Toll-Trafficking Assay

HEK293 cells were plated in 6-well cell culture treated plates in Dulbecco's Modified Eagle Medium (1×DMEM) supplemented with 10% fetal bovine serum containing no antibiotics and were maintained at 37° C., 5% CO2, and 95% relative humidity. After 24 hours, the cells (95% confluence) were transfected with pcDNA6B-Toll-Flag using Lipofectamine2000 according the manufacturer's instructions. Cells were transfected for 16 h, then were trypsinized and plated in 96-well microscopy-quality, black walled plates that had been pre-treated with attachment factor. After 3 hr incubation at 37° C. to allow the cells to attach, compound at varying concentrations in DMSO (1% DMSO final concentration) was added and cells were returned to incubator for 24 h. After 24 h, the media was removed and cells were fixed in freshly made 4% paraformaldehyde in Dulbecco's Phosphate Buffered Saline (DPBS) for 10 min at 25° C. Cells were washed twice with DPBS then stained with Wheat Germ Agglutinin-Texas Red (5 µg/mL in DPBS, 60 min, 25° C.). Cells were washed twice with DPBS, blocked in 5% bovine serum albumin (BSA, 10 min, 25° C.) followed by staining for 16 h with an anti-Toll antibody (1:200 in 5% BSA/DPBS, 4° C., Santa Cruz, sc-33741). Cells were washed twice with DPBS and stained with an anti-rabbit-AlexaFluor488 antibody (1:300 in DPBS, 25° C., Invitrogen, A-11008) for 3 h at 25° C. Cells were then washed twice with DPBS after which DAPI was added (1 μM in DPBS). Cells were imaged using an inverted Olympus IX-71 microscope with a 60× long working distance air objective using appropriate filter sets for the various tags (AlexaFluor488, Texas Red, DAPI). Images were processed using SlideBook5.0 and analyzed using CellProfiler and CellProfiler Analyst.

Western Blotting

HEK293 cells were plated in 6-well plates and treated with various concentrations of drug, GDA in DMSO (1% DMSO final concentration), or vehicle (DMSO) for 24 h. Cells were harvested in cold PBS and lysed in mammalian protein extraction reagent (MPER, Pierce) and protease inhibitors (Roche) on ice for 1 h. Lysates were clarified at 14,000 g for 10 min at 4° C. Protein concentrations were determined with the Pierce BCA assay kit per the manufacturer's instructions. Equal amounts of protein (10 μg) were electrophoresed under reducing conditions, transferred to a PVDF membrane, and immunoblotted with the corresponding specific antibodies. Membranes were incubated with an appropriate horseradish peroxidase-labeled secondary anti-body, developed with chemiluminescent substrate, and visualized.

Grp94 Immunoprecipitation

Detergent lysates of the indicated cells were immunoprecipitated with 9G10 monoclonal anti-Grp94 (StressGen, Vancouver, BC) followed by protein G-Sepharose (Sigma Chemicals or Pierce) as described in Melnick, J., Dul, J. L. & Argon, Y. Sequential interaction of the chaperones BiP and GRP94 with immunoglobulin chains in the endoplasmic reticulum. *Nature* 370, 373-375, (1994).

IGF-II Secretion

C2C12 cells (ATCC, Rockville, Md.) were induced to differentiate either by complete withdrawal of serum or by shifting to medium supplemented with 2% house serum. 17AAG at concentrations of 10-15 μM in DMSO was used to inhibit Grp94 activity. Cell growth was measured with the XTT formazan colorimetric assay (Roche), cells were grown in 3% serum, to limit the background of the assay.

For IGF-II ELISA, plates were coated with anti-IGF-II (MAb 792, R&D Systems) and incubated with the test cell media. The bound IGF-II was detected with a biotinylated anti-IGF-II antibody (BAF792, R&D Systems) and developed with streptavidin-HRP (R&D Systems) according to the manufacturer's recommended procedure. Optical density units were converted to concentrations of the growth factor with a standard curve generated with recombinant IGF-II (792-MG) (R&D Systems). Data were acquired in duplicate on a microtiter-plate reader (Dynatech Laboratories, Chantilly, Va.) at 450 nm.

Example 2

Clearance of misfolded proteins in the endoplasmic reticulum (ER) is traditionally handled by ER-associated degradation, a process that requires retro-translocation and ubiquitination mediated by a lumenal chaperone network. The inventors investigated whether the secreted, glaucoma-associated protein myocilin was processed by this pathway. Myocilin is typically transported through the ER/Golgi network, but inherited mutations in myocilin lead to its misfolding and aggregation within trabecular meshwork cells, and ultimately, ER stress-induced cell death. Using targeted knockdown strategies, the inventors determined that Grp94, the ER equivalent of Hsp90, specifically recognizes mutant myocilin, triaging it through ERAD. The addition of mutant myocilin to the short list of Grp94 clients strengthens the hypothesis that beta-strand secondary structure drives client association with Grp94.

Interestingly, the ERAD pathway is incapable of efficiently handling the removal of mutant myocilin, but when Grp94 is depleted, degradation of mutant myocilin is shunted away from ERAD towards a more robust clearance pathway for aggregation-prone proteins, the autophagy system. Thus ERAD inefficiency for distinct aggregation-prone proteins can be subverted by manipulating ER chaperones, leading to more effective clearance by the autophagic/lysosomal pathway. General Hsp90 inhibitors and a selective Grp94 inhibitor also facilitate clearance of mutant myocilin, suggesting that therapeutic approaches aimed at inhibiting Grp94 are beneficial for patients suffering from some cases of myocilin glaucoma.

The inventors evaluated the interactions of myocilin with the chaperone network and have shown that Grp94 is involved in mutant myocilin turnover. Disease-causing mutations in myocilin drive its interaction with Grp94, but this appears to facilitate an inefficient route of clearance for mutant myocilin involving ERAD that results in mutant myocilin accumulation. By depleting Grp94 either by RNA knockdown or with pharmacological agents, mutant myocilin was effectively removed through an alternative clearance pathway thus offering a new therapeutic for myocilin glaucoma.

Validation of Myocilin Inducible Cell Model

A well-established Human Embryonic Kidney (HEK) cell model that conditionally overexpresses wildtype (iWT) or I477N mutant myocilin (iI477N) was used in these studies. (Joe M K & Tomarev S I (2010) Expression of myocilin mutants sensitizes cells to oxidative stress-induced apoptosis: implication for glaucoma pathogenesis. *Am J Pathol* 176(6): 2880-2890) In this inducible and stable cell line, wildtype or I477N myocilin harbors a Flag-tag to ease downstream detection. The inventors confirmed wildtype myocilin secretion and I477N intracellular retention using dot blot analysis of the cell culture media or Western blot of the lysates, respectively (FIG. 10A). The inventors further corroborated ER retention of I477N myocilin by immunofluorescence co-localization (FIG. 10B).

Effect of siRNA-Mediated Knockdown of ER Chaperones on Myocilin5

The effects of several chaperones were evaluated in the inducible cell model using siRNA. Of the chaperones tested, which included Hsp70, Hsp40, Cdc37, Hsp90β, and Grp94, only silencing of Grp94 caused a marked reduction in intracellular I477N myocilin (FIG. 11A). (Muchowski P J & Wacker J L (2005) Modulation of neurodegeneration by molecular chaperones. *Nat Rev Neurosci* 6(1):11-22) Dot blot analysis of the media revealed a slight increase in secreted I477N myocilin upon Hsp90β and Cdc37 knockdown, whereas no secretion was observed with Grp94 knockdown (FIG. 11B). The levels of intracellular (FIG. 11C) and secreted (FIG. 11D) wildtype myocilin were not affected by knockdown of any of these chaperones.

Knockdown was confirmed for each experiment by Western blot (representative knockdown shown in FIG. 11E). This result was further validated by immunofluorescent staining for I477N myocilin in cells transfected with control or Grp94 siRNA. Grp94 knockdown reduced myocilin levels by ~63% as compared to control cells after normalization to 4',6-diamidino-2-phenylindole (DAPI) signal (FIG. 11F). This result also confirmed that Grp94 knockdown was not promoting mutant myocilin insolubility. Taken together, these results suggested that Grp94, more than other candidate chaperones, was important for regulating mutant myocilin accumulation Grp94 Preserves Mutant Myocilin.

Next, the inventors determined whether Grp94 was involved in I477N myocilin protein turnover. Cyclohexamide (CHX) chase experiments showed that the degradation rate of I477N myocilin increased ~2.5 times following Grp94 knockdown (FIG. 12A). The inventors also investigated whether Grp94 was influencing mutant myocilin solubility. This was based on previous work showing that myocilin mutants are insoluble as demonstrated by their partial retention in the stacking gel. (Yam, G. H., Gaplovska-Kysela, K., Zuber, C., and Roth, J. (2007) *Invest Ophthalmol Vis Sci* 48, 1683-1690; Zhou, Z., and Vollrath, D. (1999) *Hum Mol Genet* 8, 2221-2228) Western blot of i477N cell lysates transfected with Grp94 siRNA showed decreased insoluble myocilin as well as soluble myocilin, as detected with an antibody specific for myocilin (FIG. 12B). In contrast, overexpression of Grp94 in iI477N cells caused both soluble and insoluble mutant myocilin to accumulate (FIG. 12C).

Selective Interaction Between Grp94 and Mutant Myocilin

Figure 13:
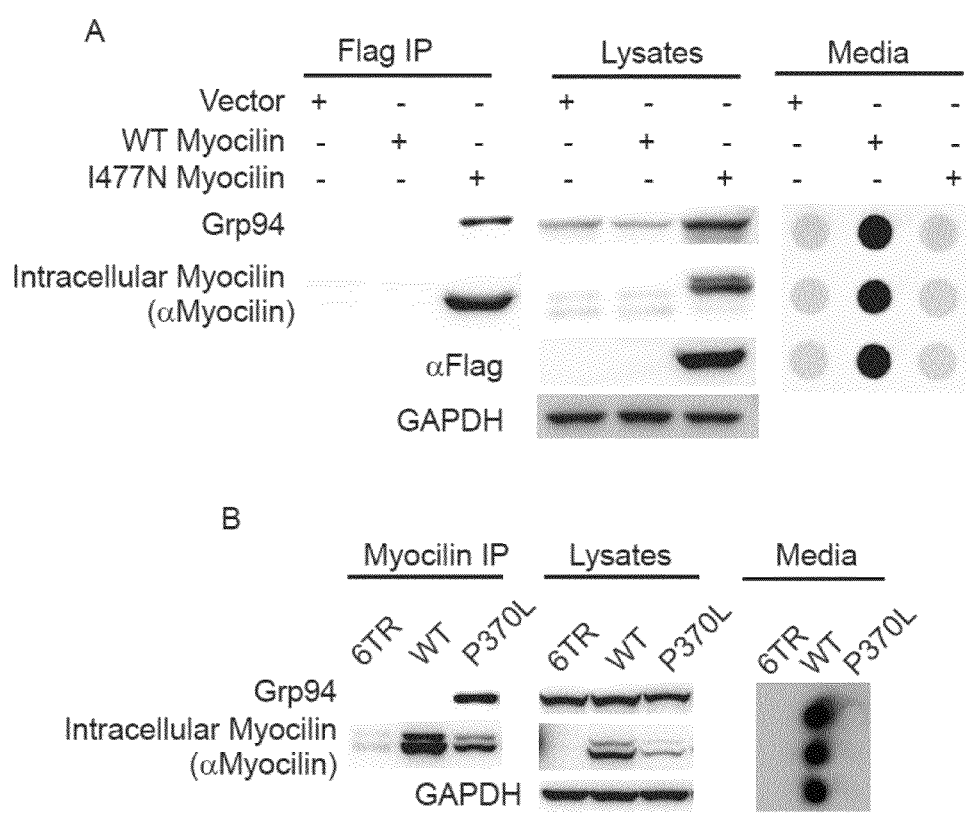

To confirm the selective interaction between Grp94 and mutant myocilin, coimmunoprecipitation assays (co-IP) were performed (FIG. 13). First, results from the stably-transfected model demonstrate that the flag-tagged I477N myocilin binds to Grp94, while wildtype myocilin does not, possibly due to its rapid secretion (FIG. 13A).

Consistent with this finding, I477N myocilin also increases Grp94 expression (FIG. 13A). To determine whether Grp94 was indeed selectively interacting with a mutant myocilin species, the inventors took advantage of the known properties of an HEK transient transfection myocilin model in which wildtype myocilin remains largely detergent soluble and is still secreted, whereas mutant myocilin is primarily detergent insoluble and thus is not secreted. (Zhou Z & Vollrath D (1999) A cellular assay distinguishes normal and mutant TIGR/myocilin protein. *Hum Mol Genet* 8(12):2221-2228; Yam G H, Gaplovska-Kysela K, Zuber C, & Roth J (2007) Sodium 4-phenylbutyrate acts as a chemical chaperone on misfolded myocilin to rescue cells from endoplasmic reticulum stress and apoptosis. *Invest Ophthalmol Vis Sci* 48(4): 1683-1690) Nevertheless, some mutant myocilin is still found in the detergent soluble fraction allowing us to directly compare the interaction between Grp94 and intracellular, soluble wildtype or mutant myocilin (FIG. 13B).

In this way, wildtype and one of the most aggressive mutant myocilin species, P370L, were transiently transfected into HEK cells and lysates were subjected to immunoprecipitation with myocilin antibody. (Ge J, Zhuo Y, Guo Y, Ming W, & Yin W (2000) Gene mutation in patients with primary open-angle glaucoma in a pedigree in China. *Chin. Med. J.* 113(3):195-197; Rozsa F W, et al. (1998) GLC1A mutations point to regions of potential functional importance on the TIGR/MYOC protein. *Mol Vis* 4:20; Adam M F, et al. (1997) Recurrent mutations in a single exon encoding the evolutionarily conserved olfactomedin-homology domain of TIGR in familial open angle glaucoma. Hum Mol Genet 6(12):2091-2097) As in the stably transfected model, wildtype myocilin does not appear to interact with Grp94 despite its robust intracellular expression, and is secreted as expected. By contrast, like I477N, the P370L myocilin variant, did associate with Grp94 (FIG. 13B).

Grp94 Attempts to Triage Mutant Myocilin Via ERAD

On the basis of the observed interaction between mutant myocilins and Grp94, the inventors speculated that Grp94 was enlisting mutant myocilin for clearance by the traditional ERAD pathway, which begins with ubiquitination in the ER lumen, and is followed by retro-translocation to the cytosol by the VCP/p97 complex for proteasomal degradation. (Ye Y, Meyer H H, & Rapoport T A (2001) The AAA ATPase Cdc48/p97 and its partners transport proteins from the ER into the cytosol. *Nature* 414(6864):652-656) The involvement of ERAD in clearance of mutant myocilin was first investigated using the transient transfection model to detect ubiquitinated myocilin.

Although in all cell samples a high level of total ubiquitinated protein is detected, as is typical following treatment with the proteasomal inhibitor epoxomicin to boost the levels of ubiquitinated protein levels for detection purposes, myocilin is only ubiquitinated in cells expressing I477N or P370L mutant myocilin (FIG. 14A). Localization of ubiquitinated I477N mutant myocilin in the ER was validated by immunofluorescence studies in the stably transfected model (FIG. 14B). In addition, the involvement of the ERAD pathway was further confirmed for the stable cell line by evaluating the effects of wildtype or dominant negative VCP/p97 (QQ VCP) transfection. This mutant form of VCP serves as a dominant negative, such that it inhibits retro-translocation of ERAD substrate. (Ye, Y., Meyer, H. H., and Rapoport, T. A. (2001) *Nature* 414, 652-656) Immunoprecipitation revealed that QQ VCP expression resulted in higher levels of ubiquitinated mutant myocilin, while wildtype VCP/p97 had minimal effect on ubiquitination (FIG. 14C). Notably, myocilin levels were somewhat higher in cells transfected with the QQ VCP compared to cells transfected with wildtype VCP/p97.

Grp94 Knockdown Enables Alternative Clearance Mechanism for Mutant Myocilin

Figure 15:
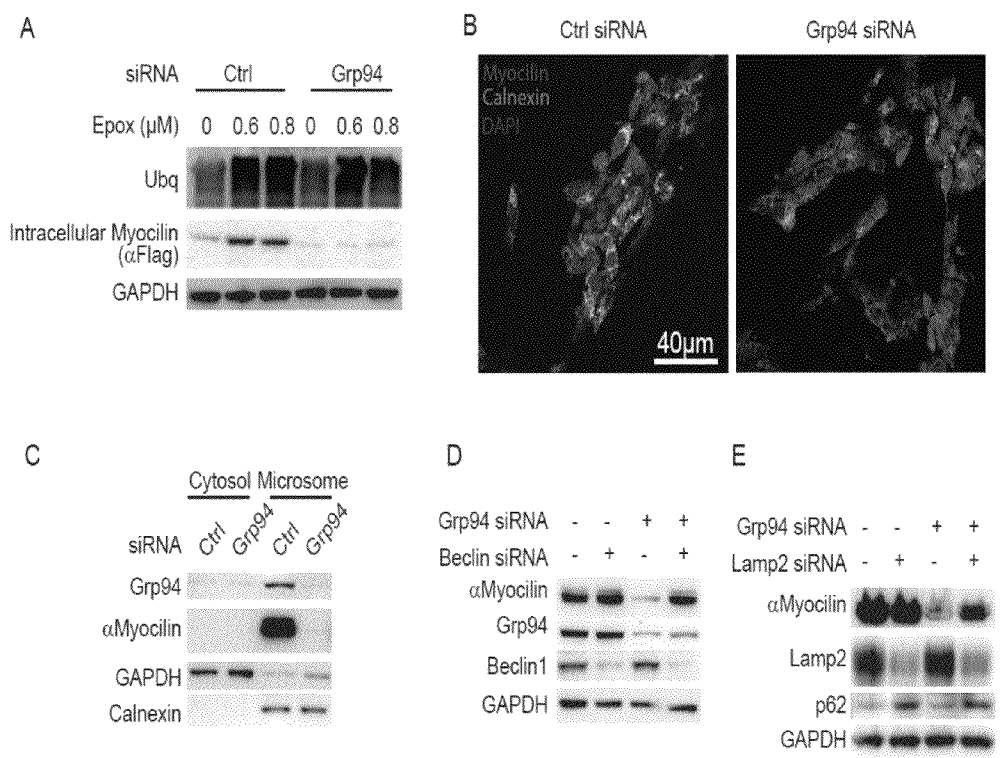

To evaluate the extent of involvement of the proteasome to degrade mutant myocilin upon Grp94 knockdown, the stable iI477N cell line was transfected with control or Grp94 siRNA and then treated with epoxomicin, a proteasome inhibitor. Although proteasome inhibition blocked the clearance of I477N myocilin under control conditions, surprisingly, there was no effect on clearance caused by Grp94 knockdown (FIG. 15A). The cellular location of mutant myocilin under conditions of Grp94 knockdown was further assessed by co-localization studies (FIG. 15B, C). Under control conditions, I477N myocilin co-localizes with the ER chaperone calnexin (FIG. 13B), whereas, under Grp94 knockdown conditions, myocilin co-localization with calnexin was diminished (FIG. 15C). While Grp94 attempts to triage I477N mutant myocilin for ERAD, Grp94 knockdown enables another, seemingly more efficient, clearance route that does not involve the proteasome.

The inventors conducted sub-cellular fractionation studies to clarify biochemically whether the localization of mutant myocilin was changing in response to Grp94 knockdown. As expected, in cells transfected with control siRNA, mutant myocilin was predominantly localized to the microsomal fraction (FIG. 15C).

In cells transfected with Grp94 siRNA, mutant myocilin was reduced in the microsomal fraction, and there was not a subsequent increase in cytosolic levels, further confirming that an alternative clearance route for mutant myocilin was being activated by Grp94 depletion (FIG. 15C). The alternative pathway being activated by Grp94 knockdown was thought to be autophagic. To determine if mutant myocilin was indeed being triaged towards autophagy after Grp94 depletion, siRNAs targeting Beclin-1 and Lamp2, two well-characterized components of the autophagic pathway, were transfected into cells along with Grp94 siRNA. Each of these has been used in cell culture extensively, including the HEK cell model used here. (Liang, X. H., Jackson, S., Seaman, M., Brown, K., Kempkes, B., Hibshoosh, H., and Levine, B. (1999) *Nature* 402, 672-676; Tanaka, Y., Guhde, G., Suter, A., Eskelinen, E. L., Hartmann, D., Lullmann-Rauch, R., Janssen, P. M., Blanz, J., von Figura, K., and Saftig, P. (2000) *Nature* 406, 902-906; Liu, H., Wang, P., Song, W., and Sun, X. (2009) *FASEB J* 23, 3383-3392; Alvarez-Erviti, L., Rodriguez-Oroz, M. C., Cooper, J. M., Caballero, C., Ferrer, I., Obeso, J. A., and Schapira, A. H. (2010) *Archives of neurology* 67, 1464-1472; Vogiatzi, T., Xilouri, M., Vekrellis, K., and Stefanis, L. (2008) *The Journal of biological chemistry* 283, 23542-23556; Chen, Y., McMillan-Ward, E., Kong, J., Israels, S. J., and Gibson, S. B. (2008) *Cell Death Differ* 15, 171-182) Indeed Beclin-1 knockdown abrogated mutant myocilin clearance caused by Grp94 depletion (FIG. 15D). Similar results were obtained when Lamp2 and Grp94 were simultaneously depleted (FIG. 15E).

Autophagy suppression was confirmed by increases in p62 levels. (Bjorkoy, G., Lamark, T., Pankiv, S., Overvatn, A., Brech, A., and Johansen, T. (2009) *Methods in enzymology* 452, 181-197) Autophagy experiments were performed four times. These findings suggest that Grp94 attempts to triage I477N mutant myocilin for ERAD, but depletion of Grp94 activates a seemingly more efficient, clearance route involving autophagy.

Pharmacological Targeting of ER Chaperones

Figure 16:
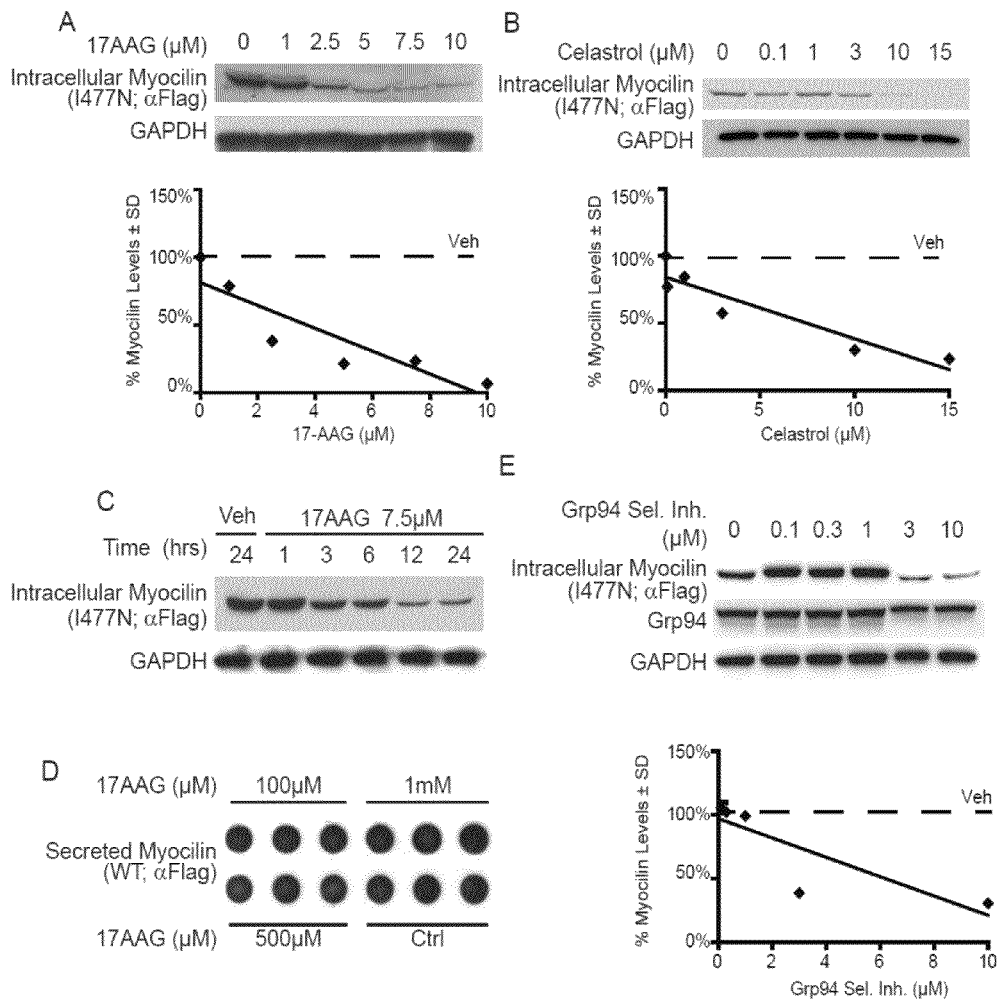

Small-molecule inhibition of Hsp90, including Grp94, is in clinical development for a number of diseases, and since Grp94 sequesters mutant myocilin from ERAD and Grp94 knockdown enables efficient clearance, the effects of Hsp90 inhibitors were tested. (Dickey C A, et al. (2007) The high-affinity HSP90-CHIP complex recognizes and selectively degrades phosphorylated tau client proteins. *J Clin Invest* 117(3):648-658; Kamal A, Boehm M F, & Burrows F J (2004) Therapeutic and diagnostic implications of Hsp90 activation. *Trends Mol Med* 10(6):283-290; Neckers L & Workman P (2012) Hsp90 molecular chaperone inhibitors: are we there yet? *Clin Cancer Res* 18(1):64-76) The stable cell lines expressing wildtype or I477N mutant myocilin were first treated with the general Hsp90/Grp94 inhibitors 17AAG or celastrol for 24 hours, resulting in dose-dependent reductions of I477N mutant myocilin (FIGS. 16A& B). 17AAG facilitated reductions in I477N myocilin as soon as 3 hours after treatment (FIG. 16C). As expected, levels of wildtype myocilin were unaffected by 17-AAG, even at a very high dose (FIG. 16D). Similarly, a Grp94-selective inhibitor reduced I477N myocilin potently at 3 and 10 µM (FIG. 16E). Lastly, YM1 (MKT-077 derivative), an inhibitor of Hsp70 proteins (including Grp78, Hsp72, Hsc70 and DnaK), did not reduce I477N. (Rousaki A, et al. (2011) Allosteric Drugs: The Interaction of Antitumor Compound MKT-077 with Human Hsp70 Chaperones. *J Mol Biol* 411(3):614-632)

Taken together, these results underscore the role of Grp94 in halting proper mutant myocilin degradation, and support the idea that both general and selective Hsp90/Grp94 inhibitors are effective therapies for glaucoma caused by mutations in myocilin.

ER stress can lead to cell death and as such has been associated with a number of diseases. (Tabas I & Ron D (2011) Integrating the mechanisms of apoptosis induced by endoplasmic reticulum stress. *Nat Cell Biol* 13(3):184-190) The protein quality control machinery can be over-zealous in triaging mutant proteins for ERAD clearance. (Meusser B, Hirsch C, Jarosch E, & Sommer T (2005) ERAD: the long road to destruction. *Nat Cell Biol* 7(8):766-772; Wang X, et al. (2006) Hsp90 co-chaperone Aha1 downregulation rescues misfolding of CFTR in cystic fibrosis. *Cell* 127(4):803-815)

For example, some mutant proteins that are folded in the ER, such as CFTR associated with cystic fibrosis, enzymes implicated in lysosomal storage disorders, the vassopresin receptor associated with nephrogenic diabetes insipidus, or rhodopsin associated with retinitis pigmintosa, retain a native-like fold when studied in vitro. Yet, their degradation via the ERAD system causes disease due to loss-of-function in the final cellular compartment. (Wang X, et al. (2006) Hsp90 co-chaperone Aha1 downregulation rescues misfolding of CFTR in cystic fibrosis. Cell 127(4):803-815; Ron I & Horowitz M (2005) ER retention and degradation as the molecular basis underlying Gaucher disease heterogeneity. *Hum Mol Genet* 14(16):2387-2398; Liou B, et al. (2006) Analyses of variant acid beta-glucosidases: effects of Gaucher disease mutations. *J Biol Chem* 281(7):4242-4253; Fan J Q, Ishii S, Asano N, & Suzuki Y (1999) Accelerated transport and maturation of lysosomal alpha-galactosidase A in Fabry lymphoblasts by an enzyme inhibitor. *Nat Med* 5(1): 112-115; Morello J P, et al. (2000) Pharmacological chaperones rescue cell-surface expression and function of misfolded V2 vasopressin receptor mutants. *J Clin Invest* 105(7):887-895; Liu X, Garriga P, & Khorana H G (1996) Structure and function in rhodopsin: correct folding and misfolding in two point mutants in the intradiscal domain of rhodopsin identified in retinitis pigmentosa. *Proc Natl Acad Sci USA* 93(10): 4554-4559; Garriga P, Liu X, & Khorana H G (1996) Structure and function in rhodopsin: correct folding and misfolding in point mutants at and in proximity to the site of the retinitis pigmentosa mutation Leu-125→Arg in the transmembrane helix C. *Proc Natl Acad Sci USA* 93(10):4560-4564) In these cases, significant efforts are in motion to rescue the mutant protein from degradation either by stabilizing it with a small molecule in the ER, or by manipulating the ER proteostasis network, with the end goal of enabling cellular trafficking and restoring activity or function in the desired cellular location. (Rajan R S, et al. (2011) Chemical and pharmacological chaperones: application for recombinant protein production and protein folding diseases. *Curr Med Chem* 18(1):1-15; Balch W E, Morimoto R1, Dillin A, & Kelly J W (2008) Adapting proteostasis for disease intervention. *Science* 319(5865): 916-919)

The case of mutant myocilin represents the opposite paradigm for ER chaperone contribution to disease. The ER protein quality control program fails to degrade mutant myocilin due to an anomalous interaction with Grp94, which leads to pathogenic consequences. (FIG. 17) The reason for aberrant Grp94 activity with mutant myocilin is not immediately clear, but it may be related to the ability of mutant myocilin to form amyloid fibrils, a non-native aggregate structure that is highly resistant to degradation, a known feature of myocilin deposits. (Zhou Z & Vollrath D (1999) A cellular assay distinguishes normal and mutant TIGR/myocilin protein. *Hum Mol Genet* 8(12):2221-2228; Orwig S D, et al. (2011) Amyloid Fibril Formation by the Glaucoma-Associated Olfactomedin Domain of Myocilin. *J Mol Biol*) The inventors found that mutant myocilin amyloids clog the ERAD pathway during attempted triage, in a process that is triggered by its interaction with Grp94.

To date, efforts to devise a treatment strategy for myocilin glaucoma have focused on increasing the secretion of mutant myocilin from the ER by the use of chemical chaperones. For example, treating cells expressing mutant myocilins or aY437H myocilin transgenic mouse with 4-phenylbutyrate (PBA) have shown some promise in increasing secretion of mutant myocilin, which results in attenuated ER stress. (Yam G H, Gaplovska-Kysela K, Zuber C, & Roth J (2007) Sodium 4-phenylbutyrate acts as a chemical chaperone on misfolded myocilin to rescue cells from endoplasmic reticulum stress and apoptosis. *Invest Ophthalmol Vis Sci* 48(4):1683-1690; Zode G S, et al. (2012) Topical ocular sodium 4-phenylbutyrate rescues glaucoma in a myocilin mouse model of primary open-angle glaucoma. *Invest. Ophthalmol. Vis. Sci.* 53(3):1557-1565) This enhanced secretion has been anecdotally attributed to increased chaperone activity; however the inventors found that increased chaperoning of mutant myocilin is at best ineffectual and at worst detrimental. Thus, combined with the fact that the OLF domain itself is not stabilized by the presence of PBA, further investigation of the mechanism of action of PBA is warranted. (Burns J N, et al. (2010) Rescue of glaucoma-causing mutant myocilin thermal stability by chemical chaperones. *ACS Chem Biol* 5(5):477-487)

While enhancing secretion is certainly a feasible strategy to treat myocilin glaucoma, the fact that myocilin knockout mice and humans carrying premature stop codons within myocilin are asymptomatic raises the possibility that treatments aimed at simply ridding TM cells of mutant myocilin is a viable therapeutic alternative. The inventors developed a novel strategy to steer mutant myocilin towards effective degradation by inhibiting Grp94.

Analogous inhibition of the paralog Hsp90 is under investigation as therapeutic strategy for many diseases including cancers and Alzheimer's disease. (Dickey C A, et al. (2007) The high-affinity HSP90-CHIP complex recognizes and selectively degrades phosphorylated tau client proteins. *J Clin Invest* 117(3):648-658; Neckers L & Workman P (2012) Hsp90 molecular chaperone inhibitors: are we there yet? *Clin Cancer Res* 18(1):64-76; Luo W, et al. (2007) Roles of heat-shock protein 90 in maintaining and facilitating the neurodegenerative phenotype in tauopathies. *Proc Natl Acad Sci USA* 104(22):9511-9516) Importantly, depletion of Grp94, while lethal during development, has no obvious consequence in adults. (Maynard J C, et al. (2010) Gp93, the *Drosophila* GRP94 ortholog, is required for gut epithelial homeostasis and nutrient assimilation-coupled growth control. *Dev Biol* 339(2):295-306) Grp94 is structurally similar to cytosolic Hsp90, but lacks known co-chaperones and has very few known clients; the limited list includes immunoglobulins, integrins and toll-like receptors. (Marzec M, Eletto D, & Argon Y (2012) GRP94: An HSP90-like protein specialized for protein folding and quality control in the endoplasmic reticulum. *Biochim Biophys Acta* 1823(3):774-787; Melnick J, Dul J L, & Argon Y (1994) Sequential interaction of the chaperones BiP and GRP94 with immunoglobulin chains in the endoplasmic reticulum. *Nature* 370(6488):373-375; Liu Y, Sweet D T, Irani-Tehrani M, Maeda N, & Tzima E (2008) Shc coordinates signals from intercellular junctions and integrins to regulate flow-induced inflammation. *J Cell Biol* 182(1):185-196; Morales C, Wu S, Yang Y, Hao B, & Li Z (2009) *Drosophila* glycoprotein 93 Is an ortholog of mammalian heat shock protein gp96 (grp94, HSP90b1, HSPC4) and retains disulfide bond-independent chaperone function for TLRs and integrins. *J Immunol* 183(8):5121-5128) Like these proteins, myocilin and in particular the OLF domain that harbors 90% of all known disease-causing lesions, contains mainly beta-strand secondary structure. (Resch Z T & Fautsch M P (2009) Glaucoma-associated myocilin: a better understanding but much more to learn. *Exp Eye Res* 88(4):704-712; Burns J N, et al. (2010) Rescue of glaucoma-causing mutant myocilin thermal stability by chemical chaperones. *ACS Chem Biol* 5(5):477-487) The addition of mutant myocilin as a Grp94 client may assist in elucidating the specific role of Grp94 in vivo.

Finally, inhibition of the proteasome under conditions of Grp94 knockdown did not arrest I477N myocilin degradation. Instead, mutant myocilin was triaged toward an autophagic pathway involving Beclin-1 and Lamp2. This suggests that strategies diverting mutant myocilin to alternative clearance pathways, such as autophagy known to be more suitable for clearing multimeric-prone proteins, are likely to be effective. (Koga H & Cuervo A M (2010) Chaperone-mediated autophagy dysfunction in the pathogenesis of neurodegeneration. *Neurobiol Dis* 43(1):29-37; Santambrogio L & Cuervo A M (2011) Chasing the elusive mammalian microautophagy. *Autophagy* 7(6):652-654) The involvement of non-ERAD clearance pathways for mutant myocilin in the absence of chaperone manipulation has already been implicated as a result of its intracellular association with peroxisomes, exosomes and lysosomes. (Shepard A R, et al. (2007) Glaucoma-causing myocilin mutants require the Peroxisomal targeting signal-1 receptor (PTS1R) to elevate intraocular pressure. *Hum Mol Genet* 16(6):609-617; Perkumas K M, Hoffman E A, McKay B S, Allingham R R, & Stamer W D (2007) Myocilin-associated exosomes in human ocular samples. *Exp Eye Res* 84(1):209-212; Hardy K M, Hoffman E A, Gonzalez P, McKay B S, & Stamer W D (2005) Extracellular trafficking of myocilin in human trabecular meshwork cells. *The Journal of biological chemistry* 280(32):28917-28926; Liton P B, Lin Y, Gonzalez P, & Epstein D L (2009) Potential role of lysosomal dysfunction in the pathogenesis of primary open angle glaucoma. *Autophagy* 5(1):122-124) When mutant myocilin is diverted away from ERAD by depleting Grp94, mutant myocilin associates with the autophagolytic system that is the pre-imminent cellular system for clearing protein aggregates. In sum, selective inhibition of Grp94, a very recent addition to the chemical biology repertoire available to regulate chaperones, is a strategy that holds considerable therapeutic promise for myocilin glaucoma.

Materials and Methods cDNA Constructs and siRNA

All myocilin cDNA constructs were a generous gift from Dr. Vincent Raymond (Laval University Hospital (CHUL) Research Center). VCP constructs were provided by Dr. Tom Rapoport (Harvard Medical School). SiRNAs were purchased from Qiagen. Where possible, a validated siRNA was used. Otherwise, two siRNAs were purchased for each gene and knockdown efficiency was tested as previously described. (Dickey C A, et al. (2007) The high-affinity HSP90-CHIP complex recognizes and selectively degrades phosphorylated tau client proteins. *J Clin Invest* 117(3):648-658) Sequences are available upon request.

Antibodies

Glyceraldehyde-3-phosphate dehydrogenase antibody was obtained from Meridian Life Science (Saco, Me.). Flag mouse monoclonal antibody was obtained from Sigma (St. Louis, Mo.). Myocilin antibody was obtained from R&D Biosystems (Minneapolis, Minn.). Calnexin antibody was obtained from Cell Signaling (Boston, Mass.). All secondary antibodies were HRP linked and obtained from Southern Biotechnologies (Birmingham, Ala.), and added at a dilution of 1:1000. Alexafluor conjugated secondary antibodies were obtained from Invitrogen (Grand Island, N.Y.).

Compounds

The selective Grp94 inhibitor was a generous gift of Dr. Brian Blagg (University of Kansas). The Hsp70/Grp78 inhibitor was a generous gift of Dr. Jason Gestwicki (University of Michigan). Epoxomicin was provided by Elan Pharmaceuticals. All compounds were solubilized in DMSO and used at concentrations that were below 1% DMSO in the final volume.

Cell Culture and Transfections

Cells were plated and grown as previously described. (Joe M K & Tomarev S I (2010) Expression of myocilin mutants sensitizes cells to oxidative stress-induced apoptosis: implication for glaucoma pathogenesis. *Am J Pathol* 176(6):2880-

2890; Jinwal U K, et al. (2009) Chemical manipulation of hsp70 ATPase activity regulates tau stability. *J Neurosci* 29(39):12079-12088) Cells were grown and maintained in Dulbecco's modified Eagle's medium supplemented with 10%, Tet system proved, fetal bovine serum (Clontech Laboratories), penicillin (100 U/ml), streptomycin (100 µg/ml), hygromycin B (200 µg/ml), and G418 (100 µg/ml) at 37° C. in 5% CO2. Inducible cells were treated with 5 ug/ul of Tetracycline to induce myocilin expression, 24 hours prior to transfection. SiRNA transfections were performed with Silentfect reagent (BioRad). DNA Transfections were performed with Lipofectamine 2000 (Invitrogen) for 48 hours. The cells were harvested in Mammalian Protein Extraction Reagent (M-PER) buffer (Pierce) containing 1× protease inhibitor mixture (Calbiochem), 100 mM phenylmethylsulfonyl fluoride, and 1× phosphatase inhibitor II and III cocktails (Sigma).

Drug Treatments

Cells were treated with Grp94 inhibitor and Hsp70/Grp78 inhibitor for 24 hours. Proteasomal inhibition was achieved by treating cells with 0.6 uM and 0.8 uM of epoxomicin.

Dot Blot

Appropriate amount of supernatant from each sample was added into each well of the dot blot apparatus, and suctioned onto a nitrocellulose membrane. The membrane was then washed with PBS (filtered) twice and placed on Ponceau S. The membrane was blocked with 7% milk and probed with myocilin or flag antibodies.

Western Blotting and Co-Immunoprecipitation

Western blot and coimmunoprecipitation analyses were performed as previously described. (Abisambra J F, et al. (2012) DnaJA1 Antagonizes Constitutive Hsp70-Mediated Stabilization of Tau. *J Mol Biol*) Protein samples were prepared using 2× Laemmli sample buffer (Bio-Rad). Samples were boiled for 5-10 min and then loaded onto a 10 well, 10% Tris-glycine gels (Invitrogen) or 18-well, 10% criterion gels (Bio-Rad). The gels were transferred onto PVDF membranes (Millipore) and then blocked for 1 hr at room temperature with 7% milk. For co-immunoprecipitations, cells were harvested with Co-IP Buffer (100 mM Tris-HCl and 150 mM NaCl) containing 1× protease inhibitor mixture(Calbiochem), 100 mM phenylmethylsulfonyl fluoride, and 1× phosphatase inhibitor II and III cocktails (Sigma). Lysates were then pre-cleared with a slurry of 20 uL of Protein G beads for 1 hr at 4° C. Pre-cleared samples were incubated with myocilin antibody for 4 hr at 4° C. 50 ul of Protein G beads were added onto the samples and incubated overnight. Samples were washed with Co-IP buffer and subjected to Western blot analysis.

Immunofluorescence and Co-Localization Studies

Tetracycline-responsive HEK cells stably transfected with myocilin and induced as described above were grown in chamber slides (Labtek). SiRNA was performed as described above. The slides were fixed with 4% paraformaldehyde and permeablized with 1% triton. Co-staining was performed with αFlag antibody (1:500 dilution) and DAPI, or αFlag, α-calnexin (1:50 dilution) and α-ubiquitin (1:50 dilution) antibodies. Appropriate AlexaFluor conjugated secondary antibodies were added at a 1:1500 dilution. DAPI was added to stain the nuclei at a 1:20,000 dilution where indicated. Slides were imaged and col llocalization analyzed with the Zeiss AxioImager.Z1 with Apotome and AxioVision software using 20×, 63×, and 100× objectives. Co-localization was assessed using the Pearson's coefficient as previously described and image intensity was assessed where indicated using ImageJ following normalization to DAPI signal. (Abisambra J F, et al. (2010) Phosphorylation dynamics regulate Hsp27-mediated rescue of neuronal plasticity deficits in tau transgenic mice. *J Neurosci* 30(46):15374-82)

Quantification and Statistical Analyses

Quantification of all blots was performed using ImageJ software as previously described. (Abisambra J F, et al. (2010) Phosphorylation dynamics regulate Hsp27-mediated rescue of neuronal plasticity deficits in tau transgenic mice. *J Neurosci* 30(46):15374-82) Graphs are plotted based on relative intensity values. Statistical analyses were performed by Student's t tests or as indicated in the figure legends.

As described herein, the inventors have demonstrated that the selective inhibition of Grp94 can be used as an effective treatment for myocilin glaucoma. The inventors have also developed selective inhibitors of Grp94 which may be used to treat myocilin glaucoma.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method for treating myocilin glaucoma in a patient comprising:
   administering a therapeutically effective amount of a Grp 94-selective inhibitor to the patient in need thereof wherein the Grp94-selective inhibitor is a compound having the formula:

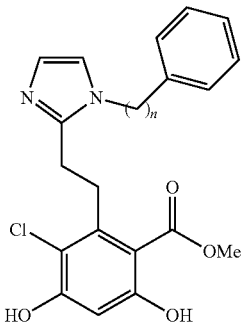

wherein n is an integer from 0 to 4.

2. The method of claim 1, wherein n is 1.

* * * * *